United States Patent
DeHennis et al.

(10) Patent No.: US 9,693,714 B2
(45) Date of Patent: Jul. 4, 2017

(54) DIGITAL ASIC SENSOR PLATFORM

(71) Applicant: Senseonics, Incorporated, Germantown, MD (US)

(72) Inventors: Andrew DeHennis, Germantown, MD (US); Arthur E. Colvin, Jr., Mt. Airy, MD (US)

(73) Assignee: Senseonics, Incorporated, Germantown, MD (US)

( * ) Notice: Subject to any disclaimer, the term of this patent is extended or adjusted under 35 U.S.C. 154(b) by 842 days.

(21) Appl. No.: 13/761,839

(22) Filed: Feb. 7, 2013

(65) Prior Publication Data
US 2013/0211213 A1 Aug. 15, 2013

Related U.S. Application Data

(60) Provisional application No. 61/597,496, filed on Feb. 10, 2012.

(51) Int. Cl.
*A61B 5/1455* (2006.01)
*A61B 5/1459* (2006.01)
(Continued)

(52) U.S. Cl.
CPC ............ *A61B 5/1455* (2013.01); *A61B 5/076* (2013.01); *A61B 5/1459* (2013.01);
(Continued)

(58) Field of Classification Search
None
See application file for complete search history.

(56) References Cited

U.S. PATENT DOCUMENTS 5,621,227 A 4/1997 Joshi
6,304,766 B1 10/2001 Colvin, Jr.
(Continued)

FOREIGN PATENT DOCUMENTS

JP H10-511815 A 11/1998
JP 2002-523774 A 7/2002
(Continued)

*Primary Examiner* — Eric Winakur
*Assistant Examiner* — Marjan Fardanesh
(74) *Attorney, Agent, or Firm* — Rothwell, Figg, Ernst & Manbeck, P.C.

(57) ABSTRACT

The present invention relates to an optical sensor that may be implanted within a living animal (e.g., a human) and may be used to measure the concentration of an analyte in a medium within the animal. The optical sensor may wirelessly receive and may be capable of bi-directional data communication. The optical sensor may include a semiconductor substrate in which various circuit components, one or more photodectors and/or a light source may be fabricated. The circuit components fabricated in the semiconductor substrate may include a comparator, an analog to digital converter, a temperature transducer, a measurement controller, a rectifier and/or a nonvolatile storage medium. The comparator may output a signal indicative of the difference between the outputs of first and second photodetectors. The measurement controller may receive digitized temperature, photodetector and/or comparator measurements and generate measurement information, which may be wirelessly transmitted from the optical sensor.

12 Claims, 23 Drawing Sheets

(51) Int. Cl.
  *A61B 5/145* (2006.01)
  *A61B 5/07* (2006.01)
  *A61B 5/00* (2006.01)

(52) U.S. Cl.
  CPC ...... *A61B 5/14532* (2013.01); *A61B 5/14551* (2013.01); *A61B 5/14552* (2013.01); *A61B 5/14556* (2013.01); *A61B 5/0031* (2013.01)

(56) References Cited

U.S. PATENT DOCUMENTS

| | | |
|---|---|---|
| 7,187,961 B2 | 3/2007 | Yamashita et al. |
| 8,932,228 B2 | 1/2015 | Sato |
| 2004/0206916 A1 | 10/2004 | Colvin, Jr. et al. |
| 2008/0108885 A1 | 5/2008 | Colvin, Jr. |
| 2008/0146890 A1* | 6/2008 | LeBoeuf ............... A61B 5/0059 600/300 |
| 2008/0221555 A1 | 9/2008 | Sheppard et al. |
| 2009/0171178 A1 | 7/2009 | He et al. |
| 2010/0024526 A1* | 2/2010 | Colvin, Jr. ......... G01N 21/6428 73/61.48 |
| 2010/0268078 A1 | 10/2010 | Scarantino et al. |
| 2011/0112389 A1 | 5/2011 | Say et al. |
| 2012/0108923 A1* | 5/2012 | Cinbis ................. A61B 5/1455 600/310 |

FOREIGN PATENT DOCUMENTS

| | | |
|---|---|---|
| JP | 2004-24551 A | 1/2004 |
| JP | 2011-200456 A | 10/2011 |

\* cited by examiner

DIGITAL ASIC SENSOR PLATFORM

CROSS-REFERENCE TO RELATED APPLICATIONS

This application claims priority to U.S. Provisional Application No. 61/597,496, filed on Feb. 10, 2012, which is incorporated by reference herein in its entirety.

BACKGROUND

Field of the Invention

The present invention relates to optical sensors and, more particularly, to optical chemical or biochemical sensors for implantation within a living animal and measurement of a concentration of an analyte in a medium within the living animal.

Description of the Background

U.S. Pat. No. 5,517,313, which is incorporated herein by reference in its entirety, describes a fluorescence-based sensing device comprising indicator molecules and a photosensitive element, e.g., a photodetector. Broadly speaking, in the context of the field of the present invention, indicator molecules are molecules where one or more optical characteristics of which is or are affected by the local presence of an analyte. In the device according to U.S. Pat. No. 5,517, 313, a light source, e.g., a light-emitting diode ("LED"), is located at least partially within a layer of material containing fluorescent indicator molecules or, alternatively, at least partially within a wave guide layer such that radiation (light) emitted by the source strikes and causes the indicator molecules to fluoresce. A high-pass filter allows fluorescent light emitted by the indicator molecules to reach the photosensitive element (photodetector) while filtering out scattered light from the light source.

The fluorescence of the indicator molecules employed in the device described in U.S. Pat. No. 5,517,313 is modulated, i.e., attenuated or enhanced, by the local presence of an analyte. For example, the orange-red fluorescence of the complex tris(4,7-diphenyl-1,10-phenanthroline)ruthenium (II) perchlorate is quenched by the local presence of oxygen. Therefore, this complex can be used advantageously as the indicator molecule in an oxygen sensor. Indicator molecules whose fluorescence properties are affected by various other analytes are known as well.

Furthermore, indicator molecules which absorb light, with the level of absorption being affected by the presence or concentration of an analyte, are also known. See, for example, U.S. Pat. No. 5,512,246, which is incorporated by reference in its entirety, which discloses compositions whose spectral responses are attenuated by the local presence of polyhydroxyl compounds such as sugars.

In the sensor described in U.S. Pat. No. 5,517,313, the material which contains the indicator molecules is permeable to the analyte. Thus, the analyte can diffuse into the material from the surrounding test medium, thereby affecting the fluorescence of the indicator molecules. The light source, indicator molecule-containing matrix material, highpass filter, and photodetector are configured such that fluorescent light emitted by the indicator molecules impacts the photodetector such that an electrical signal is generated that is indicative of the concentration of the analyte in the surrounding medium.

The sensing device described in U.S. Pat. No. 5,517,313 represents a marked improvement over devices which constitute prior art with respect to U.S. Pat. No. 5,517,313.

There has, however, remained a need for sensors that permit the detection of various analytes in the body of a living animal, e.g., a living human.

U.S. Pat. Nos. 6,330,464; 6,400,974; 6,711,423 and 7,308,292, which are incorporated herein by reference in their entireties, each describe a sensing device comprising indicator molecules and a photosensitive element that is designed for use in the human body. Despite the advancements to the state of the art represented by the sensing devices described in these patents, there still a desire for improved sensing devices.

SUMMARY

In one aspect, the present invention provides an optical sensor for implantation within a living animal and measurement of a concentration of an analyte in a medium within the living animal. The optical sensor may comprise: indicator molecules, a semiconductor substrate, a first photodetector, a second photodetector, a light source, a temperature transducer, a comparator, an analog to digital converter (ADC), an inductive element, and a measurement controller. The indicator molecules may have an optical characteristic responsive to the concentration of the analyte. The indicator molecules may be configured to interact with the analyte in the medium within the living animal when the optical sensor is implanted within the living animal. The first photodetector may be mounted on or fabricated in the semiconductor substrate and may be configured to output a first analog light measurement signal indicative of the amount of light received by the first photodetector. The second photodetector may be mounted on or fabricated in the semiconductor substrate and may be configured to output a second analog light measurement signal indicative of the amount of light received by the second photodetector. The first and second photodetectors may be symmetrically arranged relative to a center line running between the first and second photodetectors. The light source may be configured to emit excitation light to the indicator molecules from an emission point aligned on the center line running between the first and second photodetectors. The temperature transducer may be mounted on or fabricated in the semiconductor substrate and may be configured to output an analog temperature measurement signal indicative of a temperature of the optical sensor. The comparator may be fabricated in the semiconductor substrate and may be configured to output an analog light difference measurement signal indicative of a difference between the first and second analog light measurement signals. The ADC may be fabricated in the semiconductor substrate and may be configured to convert (i) the analog temperature measurement signal to a digital temperature measurement signal, (ii) the first analog light measurement signal to a first digital light measurement signal, (iii) the second analog light measurement signal to a second digital light measurement signal and (iv) the analog light difference measurement signal to a digital light difference measurement signal. The input/output circuit fabricated in the semiconductor substrate and may be configured to wirelessly transmit via the inductive element measurement information and wirelessly receive via the inductive element a measurement command and power. The measurement controller may be fabricated in the semiconductor substrate and may be configured to: (i) in accordance with the measurement command, control the light source; (ii) generate the measurement information in accordance with (a) the digital temperature measurement signal, (b) the first digital light measurement signal, (c) the second digital light measurement signal and (d) the digital light difference measurement signal; and (iii) control the input/output circuit to wirelessly transmit the measurement information.

In some embodiments, the optical sensor may be a chemical or biochemical sensor. The first and second photodetectors may be fabricated in the semiconductor substrate. The first and second photodetectors may be photodiodes that have been monolithically formed in the semiconductor substrate using a complimentary metal oxide semiconductor (CMOS) process. The optical sensor of claim 1 may comprise light source mounting pads on the semiconductor substrate. The light source mounting pads may be configured such that the light source, when mounted on the light source mounting pads, has an emission point aligned on the center line running between the first and second photodetectors. The light source may be mounted on the light source mounting pads.

In some embodiments, the optical sensor may comprise an isolation trough that electrically separates the first and second photodetectors. The optical sensor may comprise a nonvolatile storage medium fabricated in the semiconductor substrate. The nonvolatile storage medium may have stored therein measurement calibration information, and the measurement controller may be configured to control the light source in accordance with the measurement command and the measurement calibration information. The nonvolatile storage medium may have stored therein identification information, the input/output circuit may be configured to wirelessly transmit via the inductive element the identification information, and the measurement controller may be configured to control the input/output circuit to wirelessly transmit the identification information.

In some embodiments, the temperature transducer may be a band-gap based temperature transducer fabricated in the semiconductor substrate. The comparator may be a transimpedance amplifier. The input/output circuit may comprise a rectifier fabricated in the semiconductor substrate. The rectifier may be a Schottky diode. The measurement information may be digital measurement information.

In one embodiment, the indicator molecules may be signal channel indicator molecules, and the optical sensor may comprise reference channel indicator molecules configured to not interact with the analyte in the medium within the living animal when the optical sensor is implanted within the living animal. The light source may be configured to emit the excitation light to the signal channel indicator molecules and reference channel indicator molecules when turned on, the first photodetector may be configured to receive excitation light emitted by the signal channel indicator molecules, and the second photodetector may be configured to receive excitation light emitted by the reference channel indicator molecules In some embodiments, the living animal may be a living human being. The medium may be interstitial fluid or blood. The analyte may be glucose. The analyte may be oxygen. The indicator molecules may be fluorescent indicator molecules. The optical sensor may have a size and shape that permits said sensor to be implanted within the living animal, and the measurement information may be indicative of the concentration of the analyte in the medium within the living animal. The inductive element may comprise a coil. The inductive element may comprise a ferrite core, and the coil may be formed on the ferrite core.

In another aspect, the present invention provides a method of controlling an optical sensor implanted within a living animal to measure a concentration of an analyte in a medium within the living animal. The method may comprise wirelessly receiving, by way of an inductive element and an input/output circuit of the optical sensor implanted within the living animal, a measurement command and power. The input/output circuit may be fabricated in a semiconductor substrate of the optical sensor. The method may comprise, following receipt of the measurement command, turning a light source of the optical sensor on and off one or more times. The light source may be configured to, when turned on, irradiate indicator molecules having an optical characteristic responsive to the concentration of the analyte with excitation light. The indicator molecules may be configured to interact with the analyte in the medium within the living animal when the optical sensor is implanted within the living animal. The method may comprise, while the light source is turned on: (i) generating, by way of a temperature transducer mounted on or fabricated in the semiconductor substrate, a first analog temperature measurement signal indicative of a temperature of the optical sensor; (ii) generating, by way of a first photodetector mounted on or fabricated in the semiconductor substrate, a first analog light measurement signal indicative of the amount of light received by the first photodetector; (iii) generating, by way of a second photodetector mounted on or fabricated in the semiconductor substrate, a second analog light measurement signal indicative of the amount of light received by the second photodetector; and (iv) generating, by way of a comparator fabricated in the semiconductor substrate, an analog light difference measurement signal indicative of a difference between the first and second analog light measurement signals. The method may comprise, while the light source is turned off: (i) generating, by way of the temperature transducer, a second analog temperature measurement signal indicative of a temperature of the optical sensor; (ii) generating, by way of the first photodetector, a first analog ambient light measurement signal indicative of the amount of light received by the first photodetector; and (iii) generating, by way of the second photodetector, a second analog ambient light measurement signal indicative of the amount of light received by the second photodetector. The method may comprise, while the light source is turned on or turned off: (i) converting, by way of an analog to digital converter (ADC) fabricated in the semiconductor substrate, the first analog temperature measurement signal to a first digital temperature measurement signal; (ii) converting, by way of the ADC, the first analog light measurement signal to a first digital light measurement signal; (iii) converting, by way of the ADC, the second analog light measurement signal to a second digital light measurement signal; (iv) converting, by way of the ADC, the analog light difference measurement signal to a digital light difference measurement signal; (v) converting, by way of the ADC, the second analog temperature measurement signal to a second digital temperature measurement signal; (vi) converting, by way of the ADC, the first ambient analog light measurement signal to a first digital ambient light measurement signal; and (vii) converting, by way of the ADC, the second analog ambient light measurement signal to a second digital ambient light measurement signal. The method may comprise generating, by way of a measurement controller fabricated in the semiconductor substrate, measurement information in accordance with (i) the first digital temperature measurement signal, (ii) the first digital light measurement signal, (iii) the second digital light measurement signal, (iv) the digital light difference measurement signal, (v) the second digital temperature measurement signal, (vi) the first digital ambient light measurement signal and (vii) the second digital ambient light measurement signal. The method may comprise transmitting, by way of the input/output circuit and inductive element, the measurement information. The method steps may be performed while the optical sensor is implanted within the living animal, and the measurement information may be indicative of the concentration of the analyte in the medium within the living animal.

In some embodiments, the optical sensor may be a chemical or biochemical sensor. The method may comprise: reading calibration information stored in a nonvolatile storage medium fabricated in the semiconductor substrate and controlling the light source in accordance with the calibration information. The method may comprise transmitting, by way of the input/output circuit and inductive element, identification information stored in a nonvolatile storage medium fabricated in the semiconductor substrate.

In some embodiments, the method may comprise, while the light source is turned on, generating an analog light source bias measurement signal and, while the light source is turned on or turned off, converting, by way of the ADC, the analog light source bias measurement signal to a digital light source bias measurement signal. The measurement information may be generated in accordance with the digital light source bias measurement signal. The method may comprise determining, by way of a field strength measurement circuit, whether the wirelessly received power is sufficient to perform method steps.

In some embodiments, the indicator molecules may be signal channel indicator molecules, and the method may comprise irradiating the signal channel indicator molecules and reference channel indicator molecules of the optical sensor with excitation light emitted by the light source when turned on. The reference channel indicator molecules may be configured to not interact with the analyte in the medium within the living animal when the optical sensor is implanted within the living animal. The method may comprise receiving, by the first photodetector, light emitted by the signal channel indicator molecules and receiving, by the second photodetector, light emitted by the reference channel indicator molecules.

In some embodiments, the living animal may be a living human being. The medium may be interstitial fluid or blood. The analyte may be glucose. The analyte may be oxygen. The indicator molecules may be fluorescent indicator molecules.

In still another aspect, the present invention provides a sensor for implantation within a living animal and measurement of a concentration of an analyte in a medium within the living animal. The optical sensor may comprise indicator molecules, a semiconductor substrate, a photodiode, a light source, an analog to digital converter (ADC), an inductive element, an input/output circuit and a measurement controller. The indicator molecules may have an optical characteristic responsive to the concentration of the analyte. The indicator molecules may be configured to interact with the analyte in the medium within the living animal when the optical sensor is implanted within the living animal. The photodiode may be fabricated in the semiconductor substrate and may be configured to output an analog light measurement signal indicative of the amount of light received by the photodiode. The light source may be configured to emit excitation light to the indicator molecules. The analog to digital converter may be fabricated in the semiconductor substrate and may be configured to convert the analog light measurement signal to a digital light measurement signal. The input/output circuit may be fabricated in the semiconductor substrate and may be configured to wirelessly transmit via the inductive element measurement information and wirelessly receive via the inductive element a measurement command and power. The measurement controller may be fabricated in the semiconductor substrate and may be configured to: (i) in accordance with the measurement command, control the light source; (ii) generate the measurement information in accordance with the digital light measurement signal; and (iii) control the input/output circuit to wirelessly transmit the measurement information.

In some embodiments, the photodiode may have been monolithically formed in the semiconductor substrate using a complimentary metal oxide semiconductor (CMOS) process. The sensor may comprise light source mounting pads on the semiconductor substrate, and the light source may be mounted on the light source mounting pads. The sensor may comprise a nonvolatile storage medium fabricated in the semiconductor substrate.

The above and other aspects and features of the present invention, as well as the structure and application of various embodiments of the present invention, are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF THE PREFERRED EMBODIMENTS

Figure 1A:
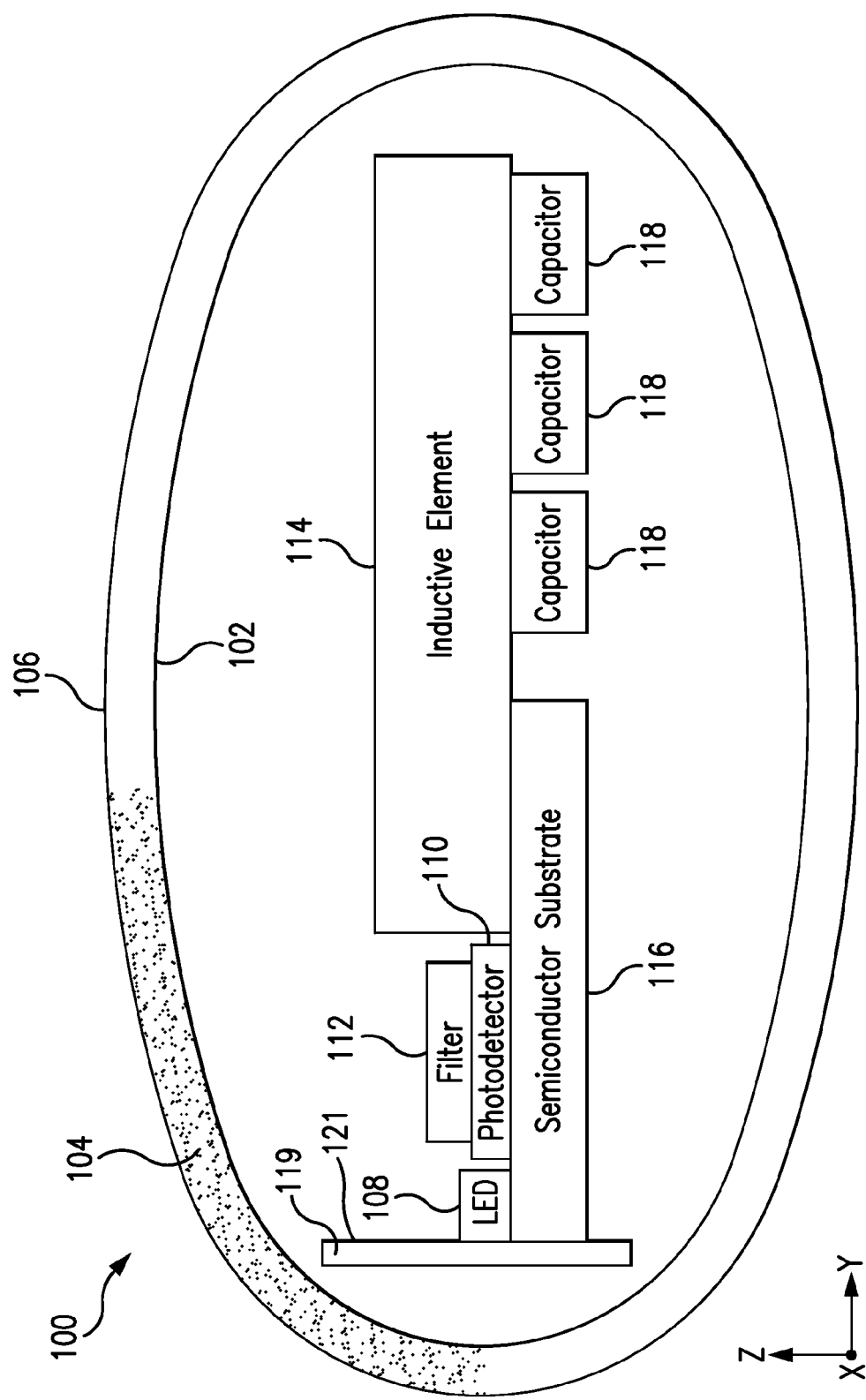
FIG. 1A is a simplified schematic, section view illustrating an optical-based sensor embodying aspects of the present invention.
Figure 1B:
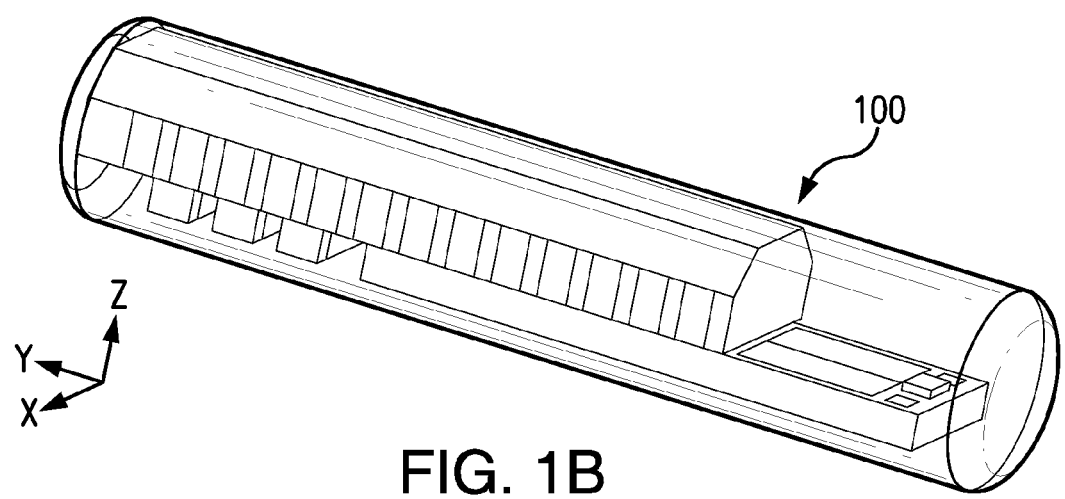
FIG. 1B-1D are a perspective view, exploded perspective view, and side view, respectively, showing the optical-based sensor in more detail.
Figure 1C:
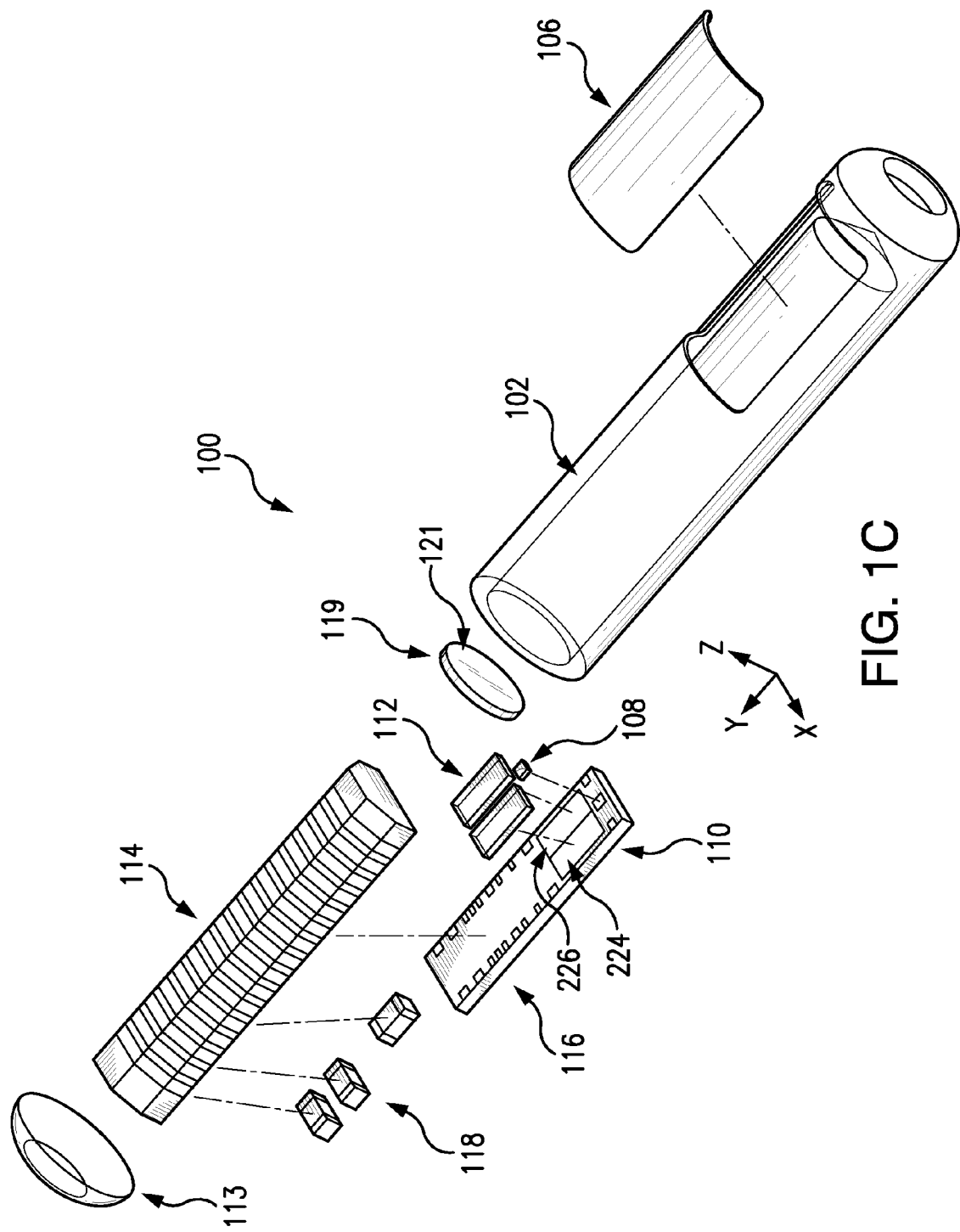
Figure 1D:
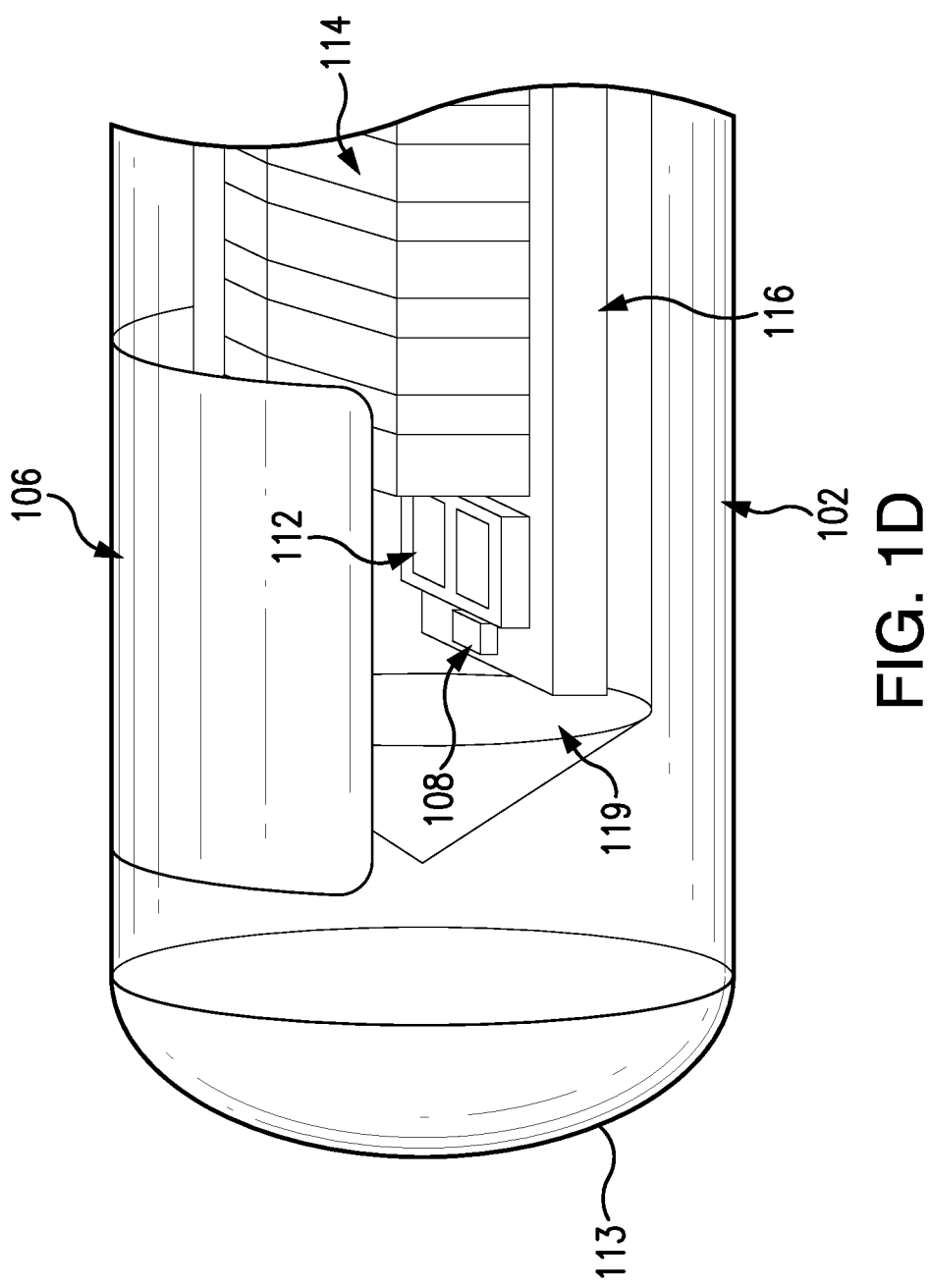

FIG. 1A is a simplified schematic, section view of an optical-based sensor ("sensor") 100 embodying aspects of the present invention. FIG. 1B-1D are a perspective view, exploded perspective view, and side view, respectively, showing the sensor 100 in more detail. In one non-limiting embodiment, sensor 100 includes a sensor housing 102 (i.e., body, shell, sleeve, or capsule). The sensor housing 102 may include an end cap 113. In exemplary embodiments, sensor housing 102 may be formed from a suitable, optically transmissive polymer material, such as, for example, acrylic polymers (e.g., polymethylmethacrylate (PMMA)).

The sensor 100 may include indicator molecules 104. Indicator molecules 104 may be fluorescent indicator molecules or absorption indicator molecules. In some non-limiting embodiments, sensor 100 may include a matrix layer 106 (i.e., graft or gel) coated on or embedded in at least a portion of the exterior surface of the sensor housing 102, with the indicator molecules 104 distributed throughout the matrix layer 106. The matrix layer 106 may cover the entire surface of sensor housing 102 (see FIG. 1A) or only one or more portions of the surface of housing 102 (see FIGS. 1C and 1D). Similarly, the indicator molecules 104 may be distributed throughout the entire matrix layer 106 or only throughout one or more portions of the matrix layer 106. Furthermore, as an alternative to coating the matrix layer 106 on the outer surface of sensor housing 102, the matrix layer 106 may be disposed on the outer surface of the sensor housing 102 in other ways, such as by deposition or adhesion.

In some embodiments including a matrix layer 106, the matrix layer 106 may comprises a biocompatible polymer matrix that is prepared according to methods known in the art and coated on the surface of the sensor housing 102. In certain embodiments, the biocompatible matrix materials are permeable to the analyte. Exemplary biocompatible matrix materials that may be used with embodiments of the invention include some methacrylates (e.g., HEMA) and hydrogels that, advantageously, can be made selectively permeable—particularly to the analyte—so as to perform a molecular weight cut-off function. In an alternative embodiment that does not include a matrix layer 106, instead of being distributed throughout a matrix layer 106, the indicator molecules 104 could simply be coated on the surface of the sensor housing 102.

In the illustrated embodiment, the sensor 100 includes a light source 108, which may be, for example, a light emitting diode (LED) or other light source, that emits radiation, including radiation over a range of wavelengths that interact with the indicator molecules 104. For example, in the case of a fluorescence-based sensor, light source 108 emits radiation at a wavelength which causes the indicator molecules 104 to fluoresce. In one non-limiting embodiment, light source 108 may be implemented using, for example, LED model number EU-U32SB from Nichia Corporation (www.nichia.com). However, other LEDs or light sources may be used depending on the specific indicator molecules applied to sensor 110 and the specific analytes of interest to be detected.

In the illustrated embodiment, sensor 100 also includes one or more photodetectors 110 (e.g., photodiodes, phototransistors, photoresistors or other photosensitive elements) which, in the case of a fluorescence-based sensor, is sensitive to fluorescent light emitted by the indicator molecules 104 such that a signal is generated by the photodetector 110 in response thereto that is indicative of the level of fluorescence of the indicator molecules.

As illustrated in FIGS. 1A, 1C, and 1D, some embodiments of sensor 100 include one or more optical filters 112, such as high pass or band pass filters. The one or more optical filters 112 may cover a photosensitive side of the one or more photodetectors 110. In one embodiment, one optical filter 112 may cover all of the one or more photodetectors 110, but, in an alternative embodiment, each of the one or more optical filters 112 may correspond to only one of the one or more photodetectors 110 and cover only the one of the one or more photodetectors 110. The one or more optical filters 112 may prevent or substantially reduce the amount of radiation generated by the light source 108 from impinging on a photosensitive side of the one or more photodetectors 110. At the same time, the one or more optical filters 112 may allow light (e.g., fluorescent light) emitted by indicator molecules 104 to pass through and strike the photosensitive side of the one or more photodetectors 110. This significantly reduces "noise" attributable to incident radiation from the light source 108 in the light measurement signals output by the one or more photodetectors 110.

As shown in FIGS. 1A and 1B, in some embodiments, sensor 100 may be wholly self-contained. In other words, the sensor may be constructed in such a way that no electrical leads extend into or out of the sensor housing 102 to supply power to the sensor (e.g., for driving the light source 108) or to transmit signals from the sensor 100. Instead, in one embodiment, the sensor 100 may be powered by an internal, self-contained power source, such as, for example, microbatteries, micro generators and/or other power sources. However, in one preferred embodiment, sensor 100 may be powered by an external power source (not shown). For example, the external power source may generate a magnetic field to induce a current in an inductive element 114 (e.g., a coil or other inductive element). Additionally, the sensor 100 may use the inductive element 114 to communicate information to an external data reader (not shown). In some embodiments, the external power source and data reader may be the same device.

In some embodiments, sensor 100 includes a semiconductor substrate 116. In the embodiment illustrated in FIGS. 1A-1D, circuitry is fabricated in the semiconductor substrate 116. The circuitry may include analog and/or digital circuitry. In a non-limiting embodiment, the circuitry may be formed in the semiconductor substrate 116 using a complimentary metal oxide semiconductor (CMOS) process. However, other formation processes (e.g., n-type metal-oxide-semiconductor (NMOS) or n-type metal-oxide-semiconductor (PMOS)) may alternatively be used.

Also, although in some preferred embodiments the circuitry is fabricated in the semiconductor substrate 116, in alternative embodiments, a portion or all of the circuitry may be mounted or otherwise attached to the semiconductor substrate 116. In other words, in alternative embodiments, a portion or all of the circuitry may include discrete circuit elements, an integrated circuit (e.g., an application specific integrated circuit (ASIC)) and/or other electronic components discrete and may be secured to the semiconductor substrate 116, which may provide communication paths between the various secured components.

In some embodiments, the one or more photodetectors 110 may be mounted on the semiconductor substrate 116, but, in some preferred embodiments, the one or more photodetectors 110 may be fabricated in the semiconductor substrate 116. For example, in a non-limiting embodiment, the one or more photodetectors 110 may be monolithically formed in the semiconductor substrate 116. For instance, in one embodiment, the one or more photodetectors 110 may be monolithically formed in the semiconductor substrate 116 using a complimentary metal oxide semiconductor (CMOS) process (e.g., using diffusions from the CMOS process). However, other formation processes (e.g., NMOS or PMOS) may alternatively be used.

In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

As shown in the embodiment illustrated in FIGS. 1A-1C, in some embodiments, the sensor 100 may include one or more capacitors 118. The one or more capacitors 118 may be, for example, one or more antenna tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, the sensor 100 may include a reflector (i.e., mirror) 119. As shown in FIGS. 1A, 1C, and 1D, reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from entering the axial end of the sensor 100. For example, in one embodiment, face 121 may have a reflective coating disposed thereon, but, in other embodiments, face 121 may be constructed from a reflective material. In some alternative embodiments, instead of being attached at an end of the semiconductor substrate 116, the reflector 119 may be mounted on the top side of the semiconductor substrate 116 (e.g., in a groove on the top side thereof).

According to one aspect of the invention, an application for which the sensor 110 was developed—although by no means the only application for which it is suitable—is measuring various biological analytes in the living body of an animal (including a human). For example, sensor 110 may be used to measure glucose, oxygen, toxins, pharmaceuticals or other drugs, hormones, and other metabolic analytes in, for example, the human body. The specific composition of the matrix layer 104 and the indicator molecules 106 may vary depending on the particular analyte the sensor is to be used to detect and/or where the sensor is to be used to detect the analyte (e.g., in the blood or subcutaneous tissues). Preferably, however, matrix layer 104, if present, should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

To facilitate use in-situ in the human body, the sensor housing 102, in one embodiment, is preferably formed in a smooth, oblong or rounded shape. Of course, other shapes and configurations could be used as well. Advantageously, in certain embodiments, the sensor 100 is on the order of approximately 500 microns to approximately 0.85 inches in length L and on the order of approximately 300 microns to approximately 0.3 inches in diameter D. In certain embodiments, the sensor 100 may have generally smooth, rounded surfaces. This configuration facilitates the sensor 100 to be implanted into the human body, i.e., dermally or into underlying tissues (including into organs or blood vessels) without the sensor interfering with essential bodily functions or causing excessive pain or discomfort. However, given its small size, the sensor 100 may have different shapes and configurations and still be implantable within a human without the sensor interfering with essential bodily functions or causing excessive pain or discomfort.

In some embodiments, a preferred length of the housing is approximately 0.5 inches to 0.85 inches and a preferred diameter is approx. 0.1 inches to 0.11 inches. However, in other embodiments, the housing may be even smaller.

Moreover, it will be appreciated that any implant placed within the human (or any other animal's) body-even an implant that is comprised of "biocompatible" materials-will cause, to some extent, a "foreign body response" within the organism into which the implant is inserted, simply by virtue of the fact that the implant presents a stimulus. In the case of a sensor, such as sensor 100, which may be implanted within the body of a living animal (e.g., a living human), the "foreign body response" is most often fibrotic encapsulation, i.e., the formation of scar tissue. Analytes (e.g., glucose and oxygen), the presence and/or concentration of which the sensor 100 may be used to detect, may have its rate of diffusion or transport hindered by such fibrotic encapsulation. This is simply because the cells forming the fibrotic encapsulation (scar tissue) can be quite dense in nature or have metabolic characteristics different from that of normal tissue.

To overcome this potential hindrance to or delay in exposing the indicator molecules 104 to biological analytes, the sensor 100 may include a sensor/tissue interface layer. The sensor/tissue interface layer may, for example, cause little or acceptable levels of fibrotic encapsulation to form. In some embodiments, the sensor/tissue interface layer may be according to any of the sensor/tissue interface layer embodiments described in U.S. Pat. No. 6,330,464, which is incorporated herein by reference in its entirety.

Figure 2A:
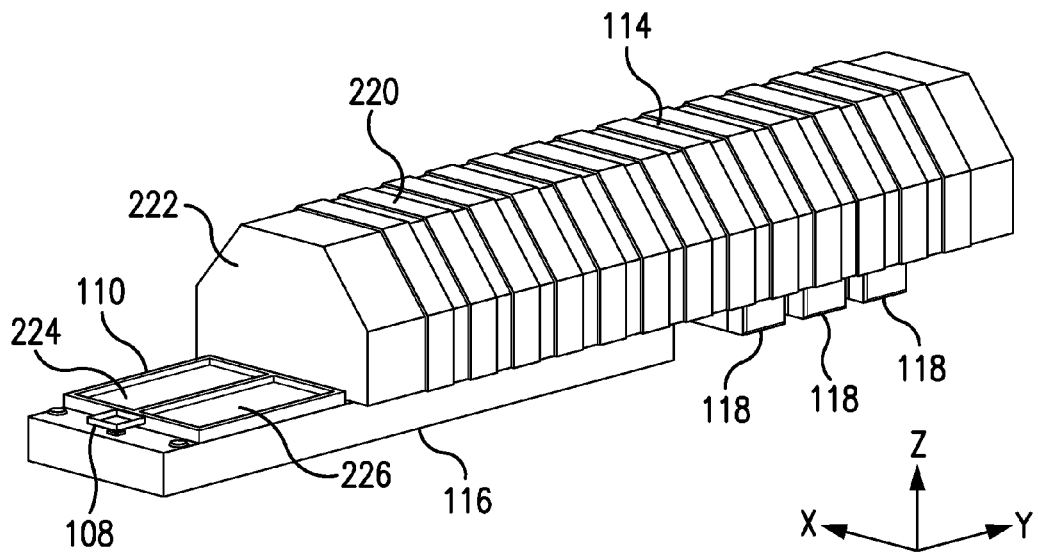
FIGS. 2A and 2B illustrate perspective views of an optical sensor embodying aspects of the present invention.
Figure 2B:
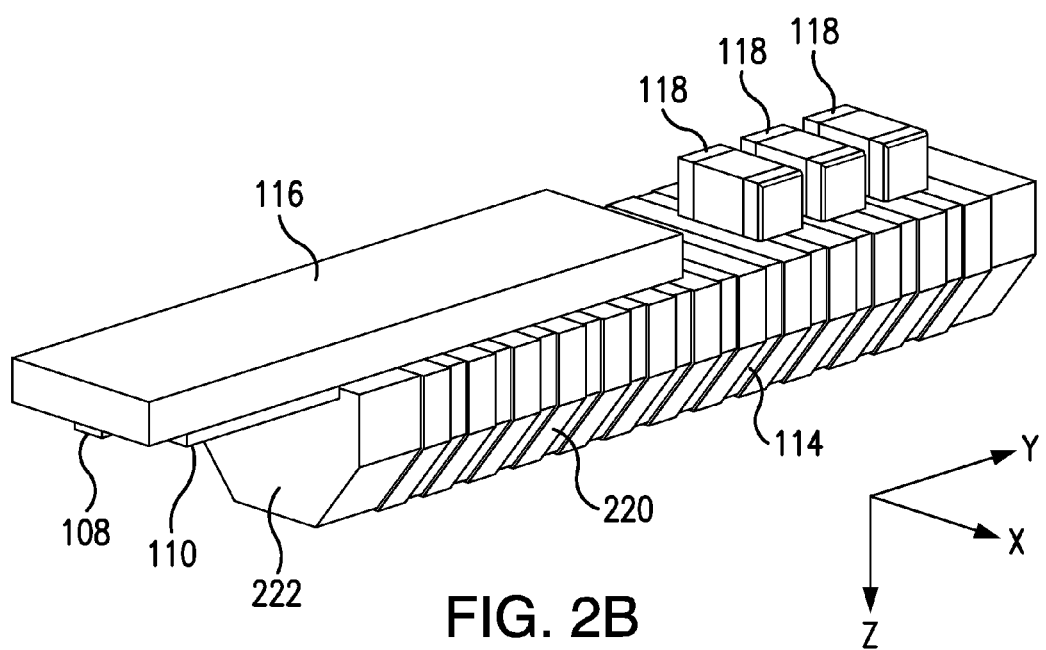

FIGS. 2A and 2B illustrate perspective views of the sensor 100. In FIGS. 2A and 2B, the reflector 119, which may be included in some embodiments of the sensor 100, is not illustrated. In the embodiment illustrated in FIGS. 2A and 2B, the inductive element 114 comprises a coil 220. In one embodiment, coil 220 may be a copper coil but other conductive materials, such as, for example, screen printed gold, may alternatively be used. In some embodiments, the coil 220 is formed around a ferrite core 222. Although core 222 is ferrite in some embodiments, in other embodiments, other core materials may alternatively be used.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which is important for implant applications, and increases cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the embodiment illustrated in FIGS. 2A and 2B, the one or more photodetectors 110 include a first photodetector 224 and a second photodetector 226. First and second photodetectors 224 and 226 may be mounted on or fabricated in the semiconductor substrate 116. In the embodiment illustrated in FIGS. 2A and 2B, sensor 100 may include one or more optical filters 112 even though they are not shown.

Figure 3A:
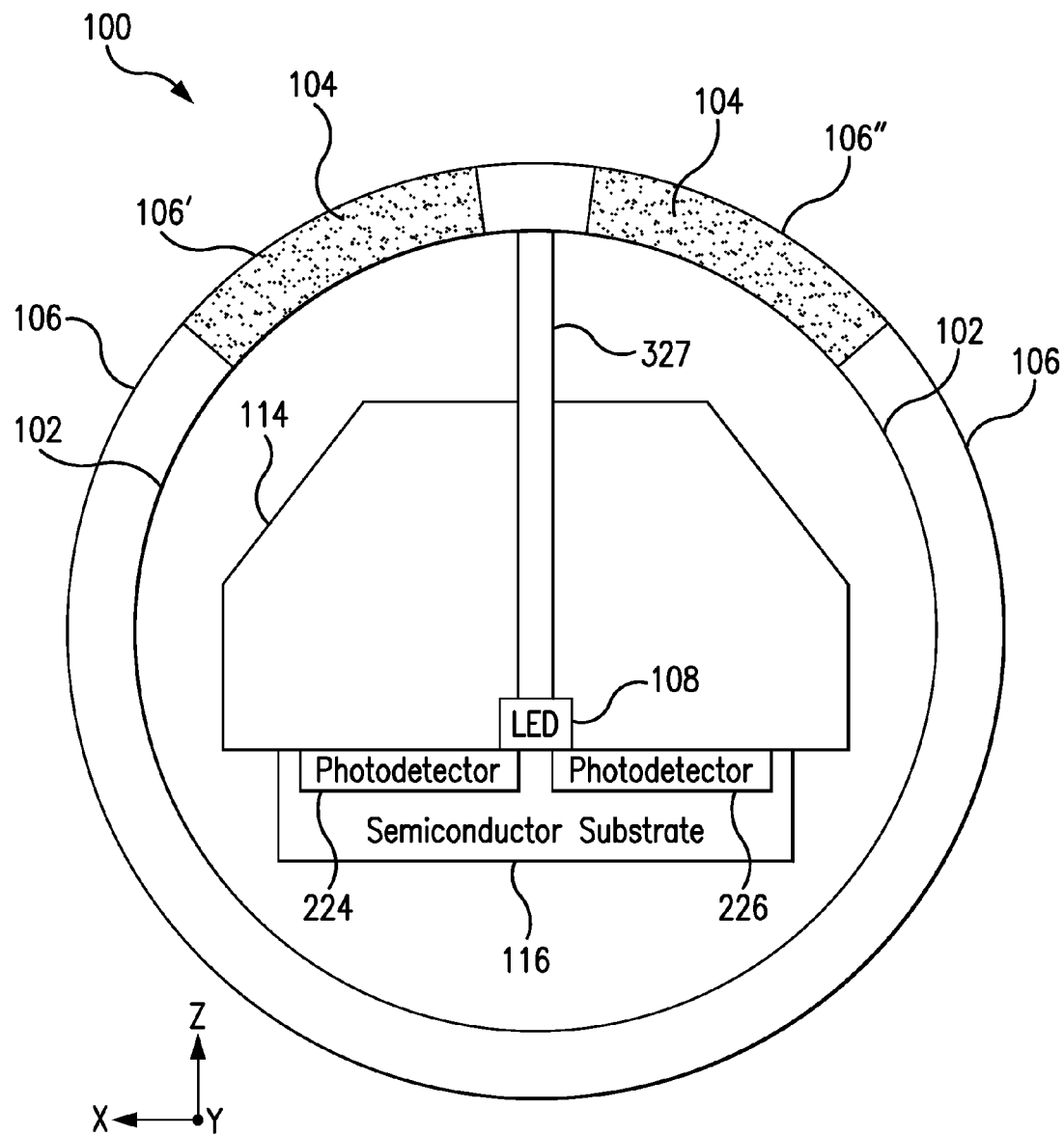
FIG. 3A illustrates a cross-sectional end view of an optical-based sensor embodying aspects of the present invention.
Figure 3B:
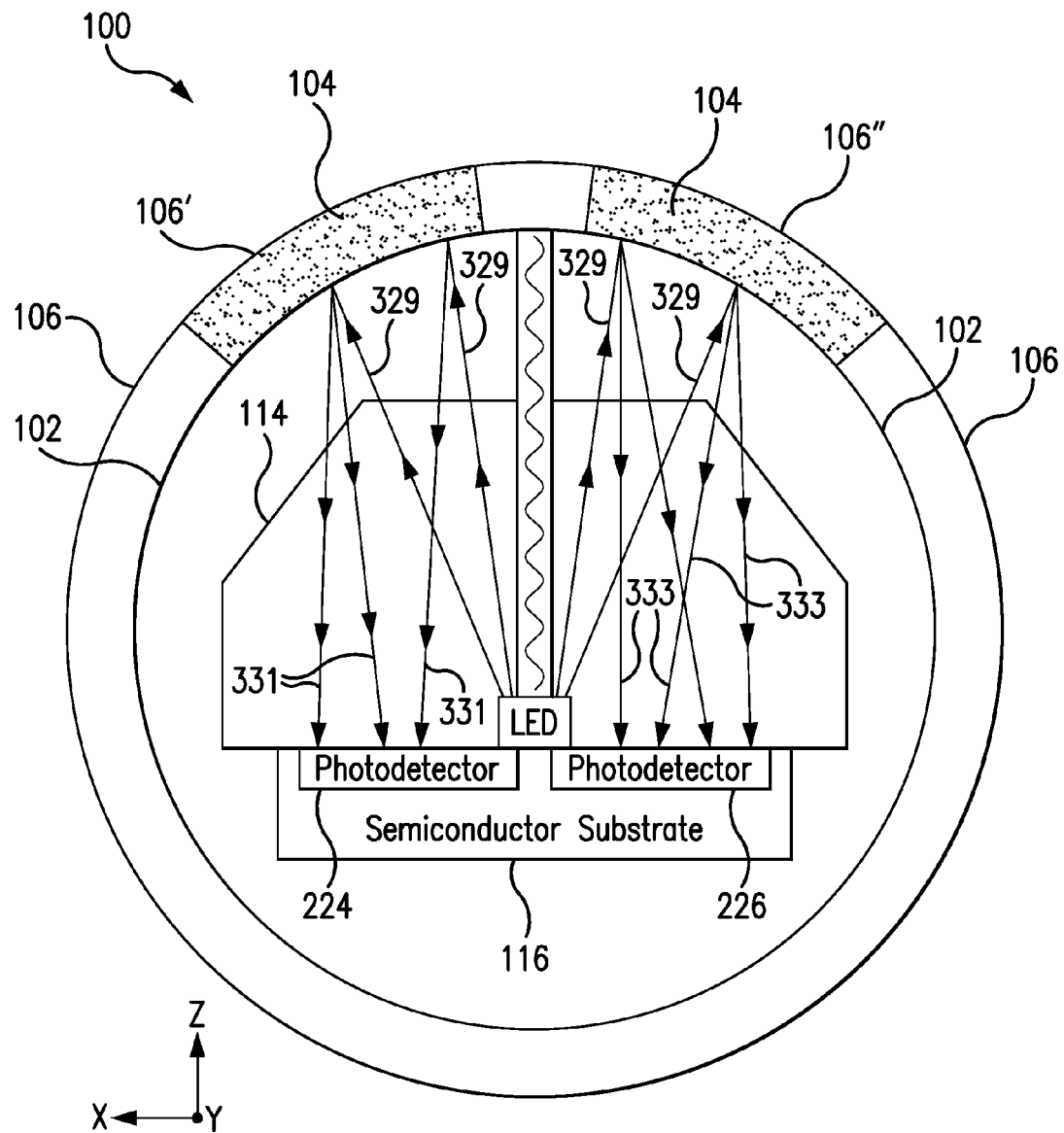
FIG. 3B illustrates a cross-sectional end view of the optical-based sensor in operation in accordance with an embodiment of the present invention.

FIGS. 3A and 3B illustrate a cross sectional end view of the sensor 100 in accordance with an embodiment of the present invention. In FIGS. 3A and 3B, the reflector 119, which may be included in some embodiments of the sensor 100, is not illustrated. As shown in FIGS. 3A and 3B, in some embodiments, the matrix layer 106 may have an indicator membrane 106' and a reference membrane 106". In a non-limiting embodiment, indicator molecules 104 sensitive to an analyte (e.g., oxygen, glucose, etc.) may be distributed throughout both the indicator membrane 106' and the reference membrane 106", the material of indicator membrane 106' may be permeable to the analyte, and the material of reference membrane 106" may be impermeable to the analyte. Thus, while the indicator molecules 104 in the indicator membrane 106' may be affected by the presence and/or concentration of the analyte, the indicator molecules 104 in the reference membrane 106" may be unaffected or generally unaffected by the presence and/or concentration of the analyte.

In some embodiments, the sensor 100 may include one or more signal channels (i.e., analyte sensing indicator channels) and one or more reference indicator channels (i.e., reference channels). In the embodiment illustrated in FIGS. 3A and 3B, the sensor 100 has a signal channel (e.g., including the indicator membrane 106' and the first photodetector 224) and a reference channel (e.g., including the reference membrane 106" and the second photodetector 226). The signal channel and the reference channel may enable the sensor 100 to obtain an indicator measurement (via the signal channel) and a reference measurement (via the reference channel). The reference measurement may be used, for example, to obtain a more accurate reading than can be obtained with the indicator measurement alone.

In operation, as shown in FIG. 3B, the light source 108 (e.g., an LED) may emit excitation light 329 that travels within the sensor housing 102 and reaches both the indicator and reference membranes 106' and 106". In a non-limiting embodiment, the excitation light 329 may cause the indicator molecules 104 distributed in indicator and reference membranes 106' and 106" to fluoresce. As the indicator membrane 106' may be permeable to the analyte in the medium (e.g., interstitial fluid (ISF) or blood) into which the sensor 100 is implanted, the indicator molecules 104 in the indicator membrane 106' may interact with the analyte in the medium and, when irradiated by the excitation light 329, may emit indicator fluorescent light 331 indicative of the presence and/or concentration of the analyte in the medium. As the reference membrane 106" may be impermeable to the analyte in the medium into which the sensor 100 is implanted, the indicator molecules 104 in the reference membrane 106" may not interact with the analyte in the medium and, when irradiated by the excitation light 329, may emit reference fluorescent light 333 that is unaffected or generally unaffected by the presence and/or concentration of the analyte in the medium. The indicator fluorescent light 331 may be received by the first photodetector 224, and the reference fluorescent light 333 may be received by the second photodetector 226.

In some embodiments, the sensor 100 may include a baffle 327, which may, for example, inhibit cross-talk of light radiated from the indicator molecules 104 in the indicator and reference membranes 106' and 106". In one embodiment, the baffle 327 may be impervious to radiation that could affect the first and second photodetectors 224 and 226 (e.g., the baffle may be painted black or the like). Also, although not shown in FIGS. 3A and 3B, the optical sensor 100 may additionally include one or more filters (e.g., one or more filters 112) that may, for example, exclude the wavelength or spectrum of light emitted by the light source 108.

In one embodiment, the indicator molecules 104 distributed in the indicator membrane 106' may be the same as the indicator molecules 104 distributed in the reference membrane 106", but, in another embodiment, the indicator molecules 104 distributed in the indicator membrane 106' may be different from the indicator molecules 104 distributed in the reference membrane 106". In addition, in one embodiment, only one type of indicator molecules 104 may be distributed in each of the indicator and reference membranes 106' and 106", but, in other embodiments, different types of indicator molecules 104 may be distributed in each of the indicator and reference membranes 106' and 106". Also, U.S. Pat. No. 6,330,464, which is incorporated herein by reference in its entirety, describes various indicator molecules for use in indicator and reference membranes and various signal and reference channel configurations, which may be incorporated into different embodiments in accordance with the present invention.

Figure 3C:
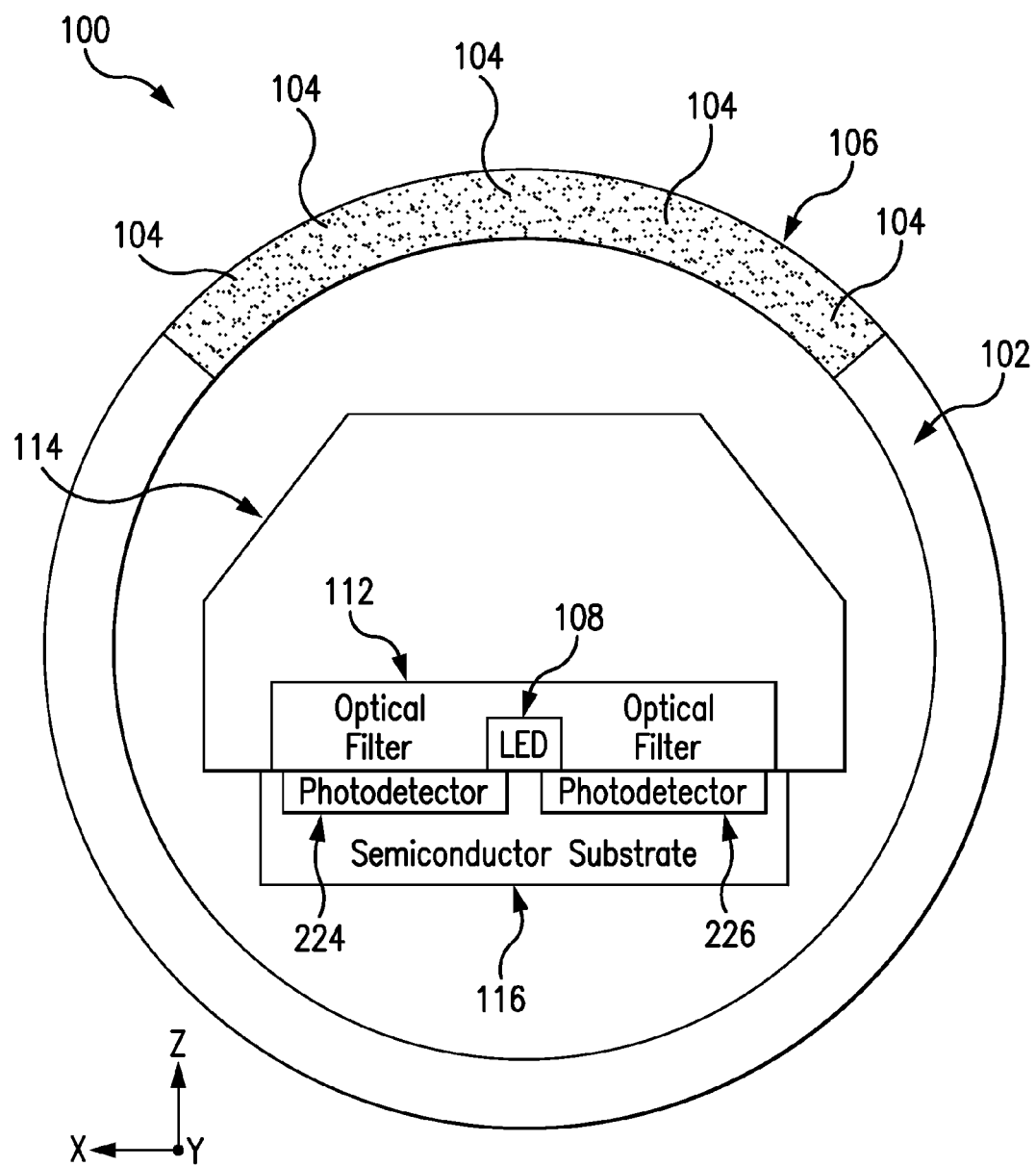
FIG. 3C illustrates a cross-sectional end view of an alternative optical-based sensor embodying aspects of the present invention.
Figure 3D:
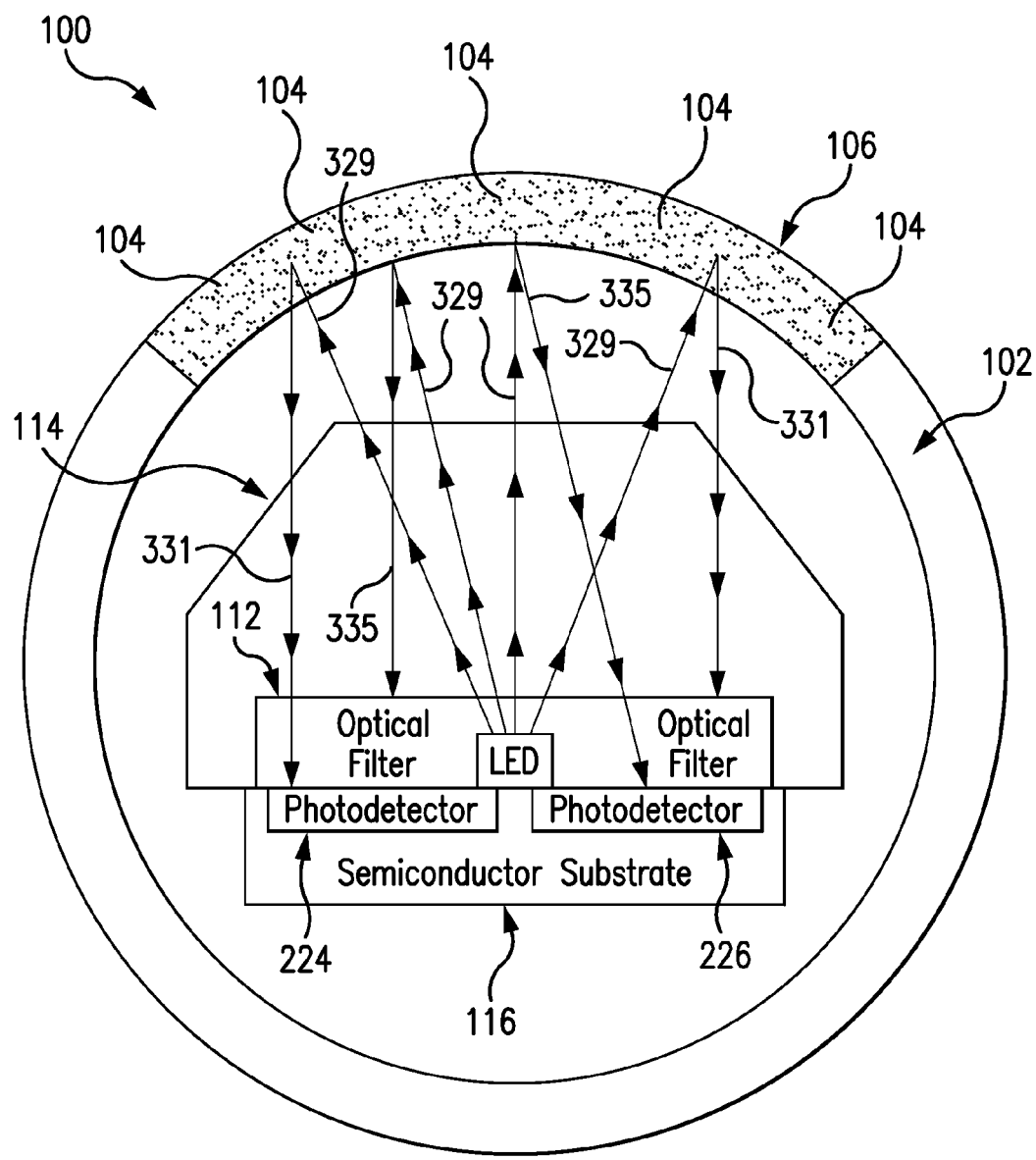
FIG. 3D illustrates a cross-sectional end view of the alternative optical-based sensor in operation in accordance with an embodiment of the present invention.

FIGS. 3C and 3D illustrate a cross sectional end view of the sensor 100 in accordance with an alternative embodiment of the present invention. In FIGS. 3C and 3D, the reflector 119, which may be included in some embodiments of the sensor 100, is not illustrated. As shown in FIGS. 3C and 3D, in some embodiments, indicator molecules 104 sensitive to an analyte (e.g., oxygen, glucose, etc.) may be distributed throughout the matrix layer/graft 106, which may be permeable to the analyte. The sensor 100 may have a signal channel (e.g., including the indicator molecules 104 and the first photodetector 224) and a reference channel (e.g., including the second photodetector 226). The signal channel and the reference channel may enable the sensor 100 to obtain an indicator measurement (via the signal channel) and a reference measurement (via the reference channel). The reference measurement may be used, for example, to obtain a more accurate reading than can be obtained with the indicator measurement alone.

In operation, as shown in FIG. 3D, the light source 108 (e.g., an LED) may emit excitation light 329 that travels within the sensor housing 102. Some of the excitation light 329 may reach the indicator molecules 104 in the matrix layer 106. Some of the excitation light 329 may be reflected from the matrix layer 106 as reflection light 335. In a non-limiting embodiment, the excitation light 329 that reaches the indicator molecules 104 may cause the indicator molecules 104 to fluoresce. The indicator molecules 104 in the matrix layer 106 may interact with the analyte in the medium and, when irradiated by the excitation light 329, may emit indicator fluorescent light 331 indicative of the presence and/or concentration of the analyte in the medium. The optical filter(s) 112, first photodetector 224, and second photodector 226 may be configured so that the first photodetector 224 (primarily) receives indicator fluorescent light 331 and the second photodector 226 (primarily) receives reflection light 335 and excitation light 329 that has reached second photodector 226 without having encountered the matrix layer 106 (e.g., excitation light 328 received directly from the light source 108 and/or received after being reflected from the sensor housing 102). For instance, in some embodiments, the optical filter(s) 112 may be configured to prevent light (e.g., reflection light 335 and excitation light 329) having the wavelength of the excitation light 329 emitted by the light source 108 from reaching the first photodetector 224 and may be configured to prevent light having the wavelength of the indicator fluorescent light 331 emitted by the indicator molecules 104 from reaching the second photodector 226.

In another alternative embodiment, both indicator molecules 104 sensitive to an analyte (e.g., oxygen, glucose, etc.) and reference indicator molecules insensitive to the analyte may be distributed throughout the matrix layer 106, which may be permeable to the analyte. In other words, while the indicator molecules 104 in the matrix layer 106 may be affected by the presence and/or concentration of the analyte, the reference indicator molecules in the matrix layer 106 may be unaffected or generally unaffected by the presence and/or concentration of the analyte. In operation, the light source 108 may emit excitation light 329 that travels within the sensor housing 102 and reaches the indicator molecules 104 and the reference indicator molecules in the matrix layer 106. The excitation light 329 may cause the indicator molecules 104 and the reference indicator molecules to fluoresce at different wavelengths. The indicator molecules 104 in the matrix layer 106 may interact with the analyte in the medium and, when irradiated by the excitation light 329, may emit indicator fluorescent light 331 indicative of the presence and/or concentration of the analyte in the medium. The reference indicator molecules in the matrix layer 106, when irradiated by the excitation light 329, may emit reference fluorescent light 333 that is unaffected or generally unaffected by the presence and/or concentration of the analyte in the medium. The optical filter(s) 112 may prevent light having the wavelength of the reference fluorescent light 333 emitted by the reference indicator molecules from reaching the first photodetector 224 and may prevent light having the wavelength of the indicator fluorescent light 331 emitted by the indicator molecules 104 from reaching the second photodector 226. The optical filters 112 may additionally prevent light having the wavelength of the excitation light 329 from reaching the first photodetector 224 and second photodector 226.

Figure 4:
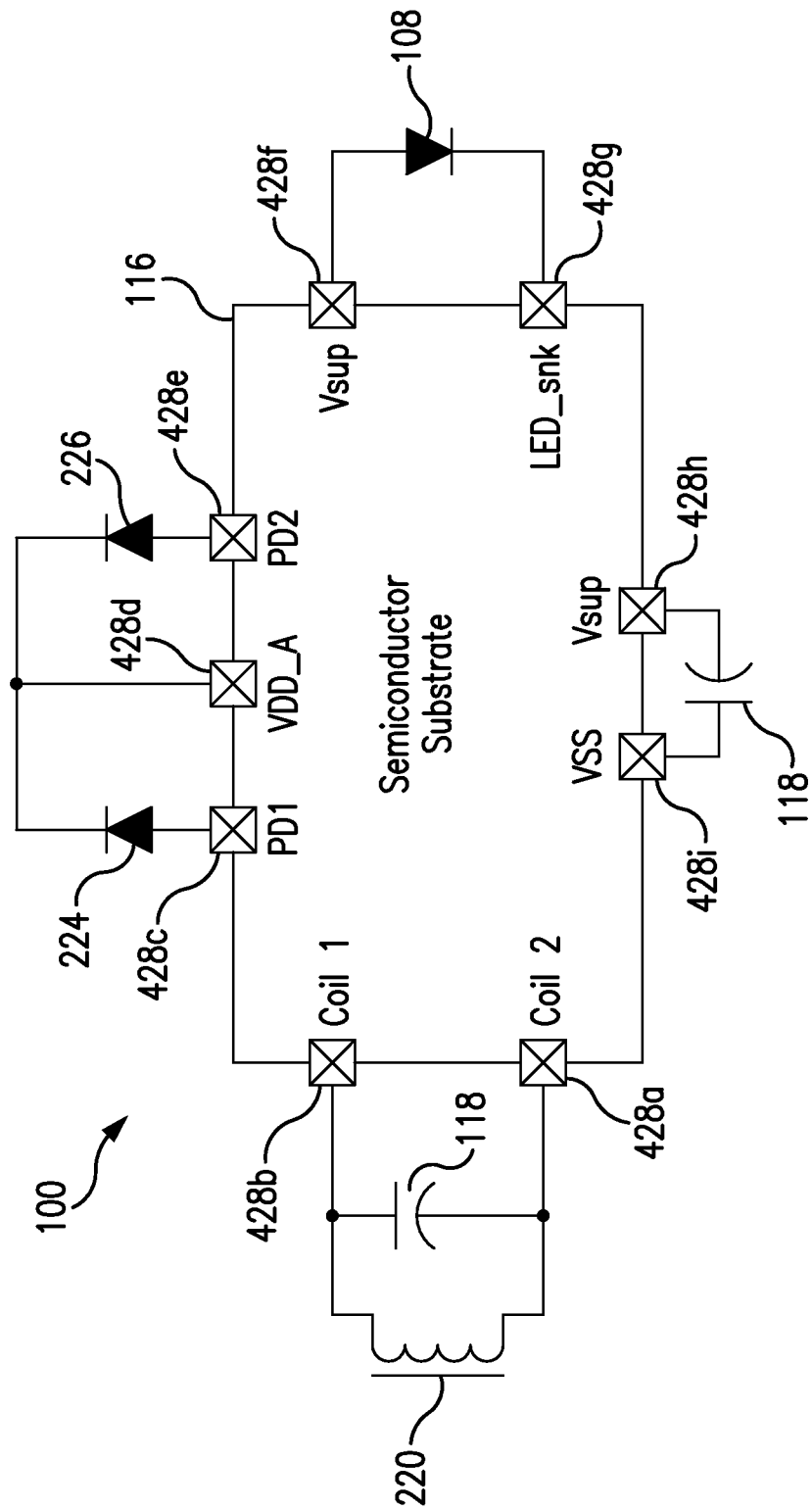
FIG. 4 is a schematic diagram illustrating the connection of external sensor components of the semiconductor substrate in accordance with an embodiment of the present invention having a coil as the inductive element.

FIG. 4 is a schematic diagram illustrating contacts (i.e., pins, pads or connections) 428 that enable external sensor components (i.e., sensor components external to the semiconductor substrate 116) to electrically connect to circuitry fabricated in the semiconductor substrate 116 according to one, non-limiting embodiment of sensor 100 having a coil 220 as the inductive element 114. As shown in FIG. 4, in some embodiments, the coil 220 may be connected to coil contacts 428a and 428b of the semiconductor substrate 116. In a non-limiting example, the coil 220 may be connected to coil contacts 428a and 428b in parallel with one or more capacitors 118, which may be one or more tuning capacitors.

As shown in FIG. 4, in some embodiments having one or more photodetectors 110, such as first and second photodetectors 224 and 226, mounted on the semiconductor substrate 116, the mounted first and second photodetectors 224 and 226 may be connected to photodetector contacts 428c, 428d and 428e in the illustrated manner. However, in embodiments having one or more photodetectors 110, such as first and second photodetectors 224 and 226, fabricated in the semiconductor substrate 116, photodetector contacts 428c, 428d and 428e may not necessary and may not be included.

As shown in FIG. 4, in some embodiments having light source 108 mounted on the semiconductor substrate 116, the mounted light source 108 may be connected to light source contacts 428f and 428g in the illustrated manner. However, in embodiments in which the light source 108 is fabricated in the semiconductor substrate 116, light source contacts 428f and 428g are not necessary and may not be included.

As shown in FIG. 4, in some embodiments, one or more capacitors 118, which may be one or more regulation capacitors, may be connected to contacts 428*h* and 428*i*. However, in other embodiments, the sensor may not include a one or more regulation capacitors, and the semiconductor substrate 116 may not include contacts 428*h* and 428*i*.

The contacts 428 illustrated in FIG. 4 are not an exhaustive list of all contacts that may be included on the semiconductor substrate 116, and the illustrated external sensor components are not an exhaustive list of all external sensor components that may connect to the semiconductor substrate 116. Some embodiments of the semiconductor substrate 116 may include one or more additional contacts 428, and, in some embodiments, one or more additional external sensor components may connect to the semiconductor substrate 116. For example, non-limiting embodiments may include one or more contacts 428 for an external temperature transducer, one or more contacts 428 that enable circuitry fabricated in the semiconductor substrate 116 to be reset and/or one or more contacts 428 that assist in testing of the circuitry fabricated in the semiconductor substrate 116 (e.g., a demodulation out contact connected to the output of a demodulator that may be fabricated in the semiconductor substrate 116). Furthermore, in some embodiments, one or more of the contacts 428 enabling electrical connection to circuitry fabricated on the semiconductor substrate 116 may have double pads. For example, in one non-limiting embodiment, all contacts 428 may have double pads.

Figure 5:
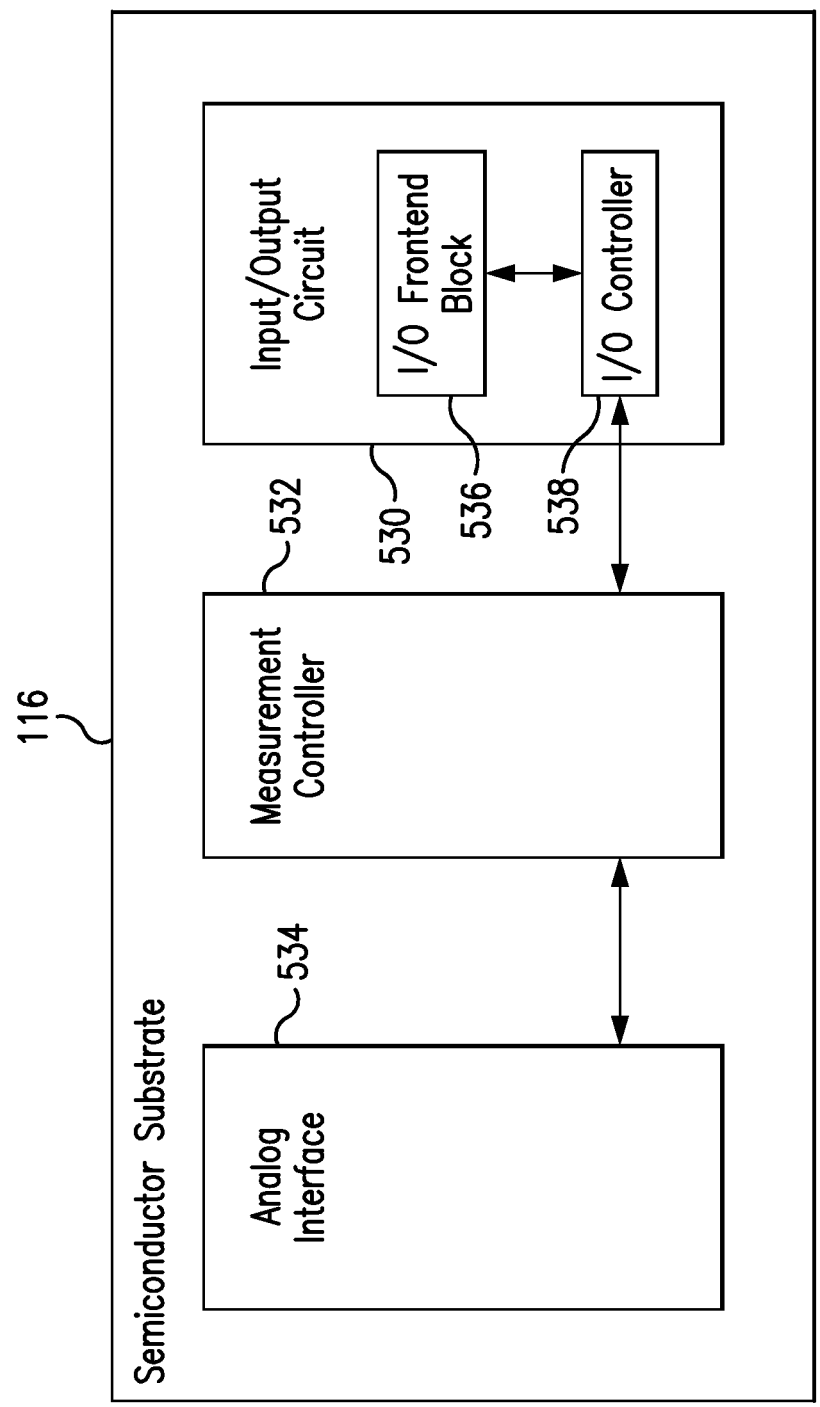
FIG. 5 is a block diagram illustrating the main functional blocks of the circuitry of an optical sensor according to an embodiment in which the circuitry is fabricated in the semiconductor substrate.

FIG. 5 is a block diagram illustrating the main functional blocks of the circuitry of sensor 100 according to an embodiment in which the circuitry is fabricated in the semiconductor substrate 116. In the embodiment illustrated in the FIG. 5, the circuitry fabricated in the semiconductor substrate 116 may include an input/output (I/O) circuit 530, measurement controller 532 and analog interface 534. The I/O circuit 530 may include an I/O frontend block 536 and an I/O controller 538.

Figure 6:
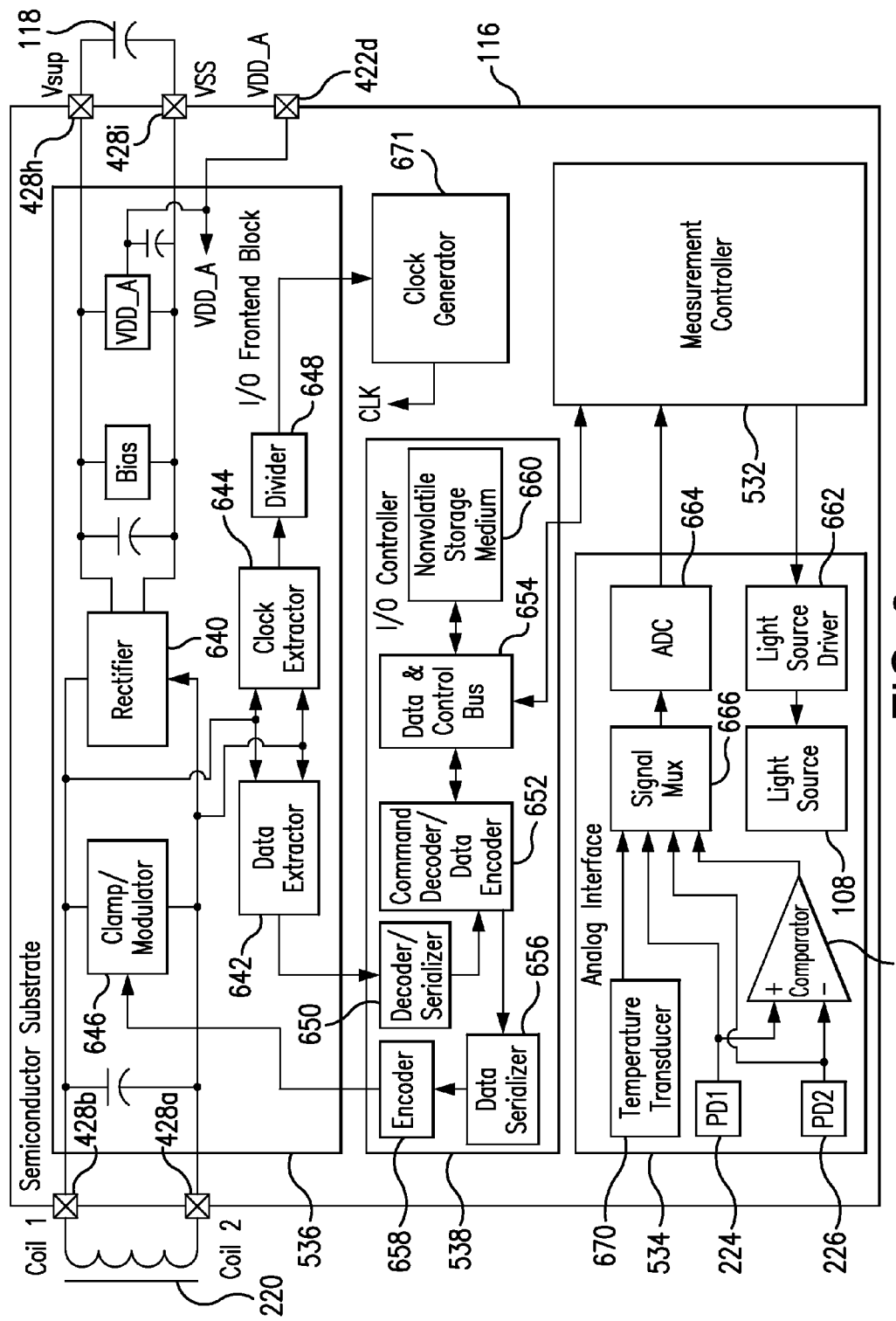
FIG. 6 is block diagram illustrating the functional blocks of the circuitry of an optical sensor according to an embodiment in which the circuitry is fabricated in the semiconductor substrate.

FIG. 6 is block diagram illustrating in more detail the functional blocks of the circuitry of sensor 100 according to a non-limiting embodiment in which the circuitry is fabricated in the semiconductor substrate 116. As shown in the embodiment of FIG. 6, in some embodiments, the I/O frontend block 536 of the I/O circuit 530 may be connected to the external inductive element 114, which may be in the form of a coil 220, through coil contacts 428*a* and 428*b*. The I/O frontend block 536 may include a rectifier 640, a data extractor 642, a clock extractor 644, clamp/modulator 646 and/or frequency divider 648. Data extractor 642, clock extractor 644 and clamp/modulator 646 may each be connected to external coil 220 through coil contacts 428*a* and 428*b*. The rectifier 640 may convert an alternating current produced by coil 220 to a direct current that may be used to power the sensor 100. For instance, the direct current may be used to produce one or more voltages, such as, for example, voltage VDD_A, which may be used to power the one or more photodetectors 110. In one non-limiting embodiment, the rectifier 640 may be a Schottky diode; however, other types of rectifiers may be used in other embodiments. The data extractor 642 may extract data from the alternating current produced by coil 220. The clock extractor 644 may extract a signal having a frequency (e.g., 13.56 MHz) from the alternating current produced by coil 220. The frequency divider 648 may divide the frequency of the signal output by the clock extractor 644. For example, in a non-limiting embodiment, the frequency divider 648 may be a 4:1 frequency divider that receives a signal having a frequency (e.g., 13.56 MHz) as an input and outputs a signal having a frequency (e.g., 3.39 MHz) equal to one fourth the frequency of the input signal. The outputs of rectifier 640 may be connected outputs of rectifier 640 may be connected to one or more external capacitors 118 (e.g., one or more regulation capacitors) through contacts 428*h* and 428*i*.

In some embodiments, the I/O controller 538 of the I/O circuit 530 may include a decoder/serializer 650, command decoder/data encoder 652, data and control bus 654, data serializer 656 and/or encoder 658. The decoder/serializer 650 may decode and serialize the data extracted by the data extractor 642 from the alternating current produced by coil 220. The command decoder/data encoder 652 may receive the data decoded and serialized by the decoder/serializer 650 and may decode commands therefrom. The data and control bus 654 may receive commands decoded by the command decoder/data encoder 652 and transfer the decoded commands to the measurement controller 532. The data and control bus 654 may also receive data, such as measurement information, from the measurement controller 532 and may transfer the received data to the command decoder/data encoder 652. The command decoder/data encoder 652 may encode the data received from the data and control bus 654. The data serializer 656 may receive encoded data from the command decoder/data encoder 652 and may serialize the received encoded data. The encoder 658 may receive serialized data from the data serializer 656 and may encode the serialized data. In a non-limiting embodiment, the encoder 658 may be a Manchester encoder that applies Manchester encoding (i.e., phase encoding) to the serialized data. However, in other embodiments, other types of encoders may alternatively be used for the encoder 658, such as, for example, an encoder that applies 8B/10B encoding to the serialized data.

The clamp/modulator 646 of the I/O frontend block 536 may receive the data encoded by the encoder 658 and may modulate the current flowing through the inductive element 114 (e.g., coil 220) as a function of the encoded data. In this way, the encoded data may be transmitted wirelessly by the inductive element 114 as a modulated electromagnetic wave. The wirelessly transmitted data may be detected by an external reading device by, for example, measuring the current induced by the modulated electromagnetic wave in a coil of the external reading device. Furthermore, by modulating the current flowing through the coil 220 as a function of the encoded data, the encoded data may be transmitted wirelessly by the coil 220 as a modulated electromagnetic wave even while the coil 220 is being used to produce operating power for the sensor 100. See, for example, U.S. Pat. Nos. 6,330,464 and 8,073,548, which are incorporated herein by reference in their entireties and which describe a coil used to provide operative power to an optical sensor and to wirelessly transmit data from the optical sensor. In some embodiments, the encoded data is transmitted by the sensor 100 using the clamp/modulator 646 at times when data (e.g., commands) are not being received by the sensor 100 and extracted by the data extractor 642. For example, in one non-limiting embodiment, all commands may be initiated by an external sensor reader (e.g., sensor 1500 of FIG. 15) and then responded to by the sensor 100 (e.g., after or as part of executing the command). In some embodiments, the communications received by the inductive element 114 and/or the communications transmitted by the inductive element 114 may be radio frequency (RF) communications. Although, in the illustrated embodiments, the sensor 100 includes a single coil 220, alternative embodiments of the sensor 100 may include two or more coils (e.g., one coil for data transmission and one coil for power and data reception).

In an embodiment, the I/O controller 538 may also include a nonvolatile storage medium 660. In a non-limiting embodiment, the nonvolatile storage medium 660 may be an electrically erasable programmable read only memory (EEPROM). However, in other embodiments, other types of nonvolatile storage media, such as flash memory, may be used. The nonvolatile storage medium 660 may receive write data (i.e., data to be written to the nonvolatile storage medium 660) from the data and control bus 654 and may supply read data (i.e., data read from the nonvolatile storage medium 660) to the data and control bus 654. In some embodiments, the nonvolatile storage medium 660 may have an integrated charge pump and/or may be connected to an external charge pump. In some embodiments, the nonvolatile storage medium 660 may store identification information (i.e., traceability or tracking information), measurement information and/or setup parameters (i.e., calibration information). In one embodiment, the identification information may uniquely identify the sensor 100. The unique identification information may, for example, enable full traceability of the sensor 100 through its production and subsequent use. In one embodiment, the nonvolatile storage medium 660 may store calibration information for each of the various sensor measurements.

In some embodiments, the analog interface 534 may include a light source driver 662, analog to digital converter (ADC) 664, a signal multiplexer (MUX) 666 and/or comparator 668. In a non-limiting embodiment, the comparator 668 may be a transimpedance amplifier, in other embodiments, different comparators may be used. The analog interface 534 may also include light source 108, one or more photodetectors 110 (e.g., first and second photodetectors 224 and 226) and/or a temperature transducer 670. In a non-limiting, exemplary embodiment, the temperature transducer 670 may be a band-gap based temperature transducer. However, in alternative embodiments, different types of temperature transducers may be used, such as, for example, thermistors or resistance temperature detectors. Furthermore, like the light source 108 and one or more photodetectors 110, in one or more alternative embodiments, the temperature transducer 670 may be mounted on semiconductor substrate 116 instead of being fabricated in semiconductor substrate 116.

The light source driver 662 may receive a signal from the measurement controller controller 532 indicating the light source current at which the light source 108 is to be driven, and the light source driver 662 may drive the light source 108 accordingly. The light source 108 may emit radiation from an emission point in accordance with a drive signal from the light source driver 662. The radiation may excite indicator molecules 104 distributed throughout a matrix layer 106 coated on at least part of the exterior surface of the sensor housing 102. The one or more photodetectors 110 (e.g., first and second photodetectors 224 and 226) may each output an analog light measurement signal indicative of the amount of light received by the photodetector. For instance, in the embodiment illustrated in FIG. 6, the first photodetector 224 may output a first analog light measurement signal indicative of the amount of light received by the first photodetector 224, and the second photodetector 226 may output a first analog light measurement signal indicative of the amount of light received by the second photodetector 226. The comparator 668 may receive the first and second analog light measurement signals from the first and second photodetectors 224 and 226, respectively, and output an analog light difference measurement signal indicative of the difference between the first and second analog light measurement signals. The temperature transducer 670 may output an analog temperature measurement signal indicative of the temperature of the sensor 100. The signal MUX 666 may select one of the analog temperature measurement signal, the first analog light measurement signal, the second analog light measurement signal and the analog light difference measurement signal and may output the selected signal to the ADC 664. The ADC 664 may convert the selected analog signal received from the signal MUX 666 to a digital signal and supply the digital signal to the measurement controller 532. In this way, the ADC 664 may convert the analog temperature measurement signal, the first analog light measurement signal, the second analog light measurement signal and the analog light difference measurement signal to a digital temperature measurement signal, a first digital light measurement signal, a second digital light measurement signal and a digital light difference measurement signal, respectively, and may supply the digital signals, one at a time, to the measurement controller 532.

In some embodiments, the analog interface 534 may also include a backscatter functionality. For example, in one embodiment, the backscatter functionality may be implemented by impedance modulation through a loosely coupled transformer. The impedance may be modulated by changing the power loading of circuitry in the sensor 100.

In some embodiments, the circuitry of sensor 100 fabricated in the semiconductor substrate 116 may additionally include a clock generator 671. The clock generator 671 may receive, as an input, the output of the frequency divider 648 and generate a clock signal CLK. The clock signal CLK may be used by one or more components of one or more of the I/O fronted block 536, I/O controller 538, measurement controller 532 and analog interface 534. In a non-limiting embodiment, the clock signal CLK may have a frequency of 1.13 MHz, but, in other embodiments, other frequencies may be used.

In a non-limiting embodiment, data (e.g., decoded commands from the command decoder/data encoder 652 and/or read data from the nonvolatile storage medium 660) may be transferred from the data and control bus 654 of the I/O controller 538 to the measurement controller 532 via transfer registers and/or data (e.g., write data and/or measurement information) may be transferred from the measurement controller 532 to the data and control bus 654 of the I/O controller 538 via the transfer registers.

In some embodiments, the circuitry of sensor 100 may include a field strength measurement circuit. In embodiments, the field strength measurement circuit may be part of the input/output circuit 530 or the measurement controller 532 or may be a separate functional component. The field strength measurement circuit may measure the received (i.e., coupled) power (e.g., in mWatts). The field strength measurement circuit may detect whether the received power is sufficient to run the sensor 100. For example, the field strength measurement circuit may detect whether the received power is sufficient to produce a certain voltage and/or current. In one non-limiting embodiment, the field strength measurement circuit may detect whether the received power produces a voltage of at least approximately 3V and a current of at least approximately 0.5 mA. However, other embodiments may detect that the received power receives produces at least a different voltage and/or at least a different current.

Figure 7:
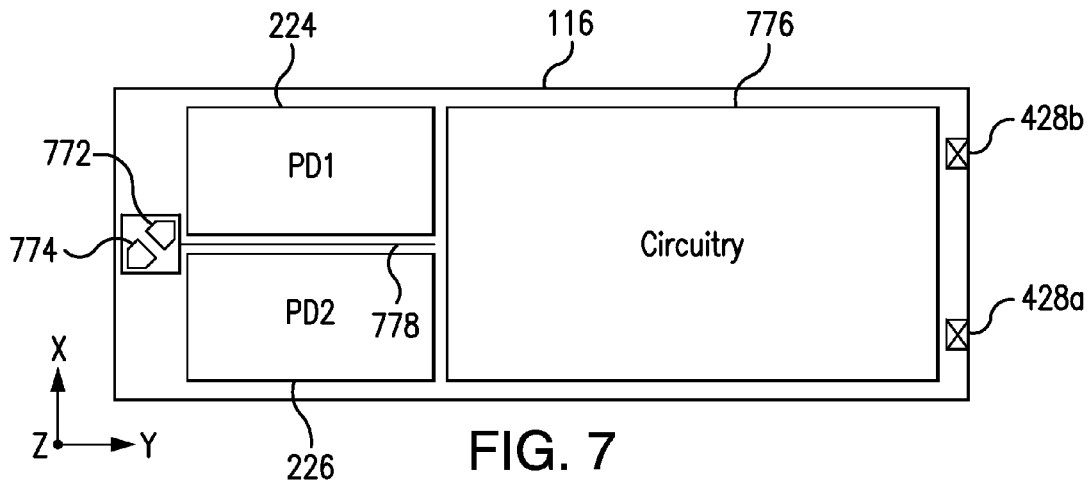
FIG. 7 illustrates the layout of a semiconductor substrate in accordance with an embodiment of the present invention.

FIG. 7 illustrates the layout of a semiconductor substrate 116 according to an embodiment of the present invention. In the embodiment shown in FIG. 7, first and second photodetectors 224 and 226 are fabricated in the semiconductor substrate 116, and the semiconductor substrate 116 has light source mounting pads 772 and 774 for mounting light source 108. In one embodiment, light source mounting pads 772 and 774 may connect to the anode and cathode, respectively, of a light source 108 mounted on the semiconductor substrate 116. In FIG. 7, the input/output (I/O) circuit 530, measurement controller 532 and analog interface 534 (other than first and second photodetectors 224 and 226 and light source 108) is shown as circuitry 776. In the embodiment shown in FIG. 7, the circuitry 776 is fabricated in the semiconductor substrate 116.

In non-limiting embodiments, the semiconductor substrate 116 may include an isolation trough 778. The isolation trough 778 may isolate and electrically separate the first and second photodetectors 224 and 226. In one embodiment, the isolation trough 778 may be formed on a center line running between the first and second photodetectors 224 and 226. Also, in some embodiments, the light source mounting pads 772 and 774 may be configured such that the emission point of light source 108, when mounted on the light source mounting pads 772 and 774, is aligned on the center line running between the first and second photodiodes 224 and 226. Similarly, in some embodiments in which the light source 108 is fabricated in the silicon substrate 116, the emission point of the fabricated light source 108 is aligned on the center line running between the first and second photodiodes 224 and 226. In some embodiments, the fabrication of symmetrical photodetectors 224 and 226 (i.e., photodetectors which are symmetrical relative to the light source emission point) may realize dual channels that are closer to being identical to each other than can be achieved by using discrete parts (e.g., photodetectors mounted on the semiconductor substrate 116). The nearly identical photodetector channels may improve the accuracy of the sensor measurements. This may be especially true when, in some embodiments, the nearly identical dual photodetector channels are utilized as a signal channel and a reference channel, respectively.

Figure 8:
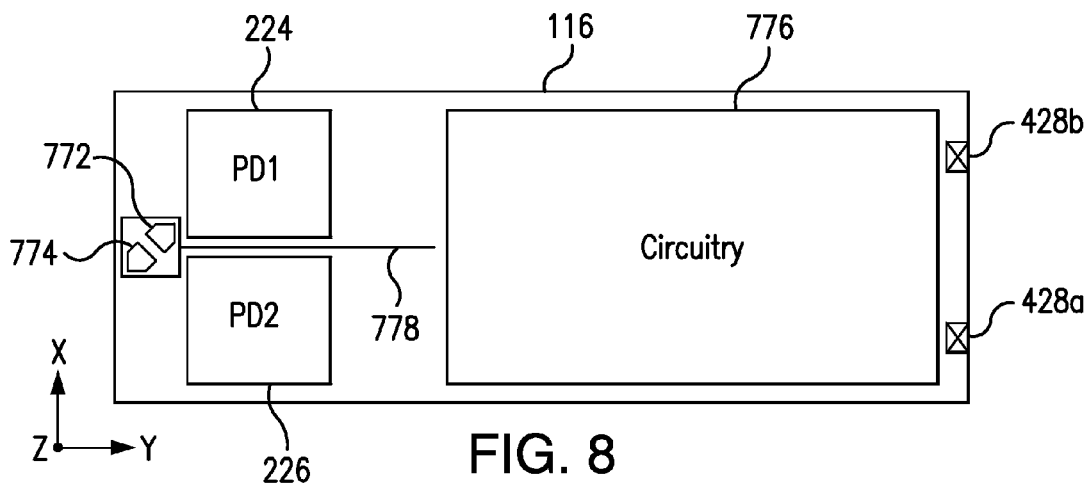
FIGS. 8 and 9 illustrate alternative layouts of a semiconductor substrate in accordance with exemplary alternative embodiments of the present invention.
Figure 9:
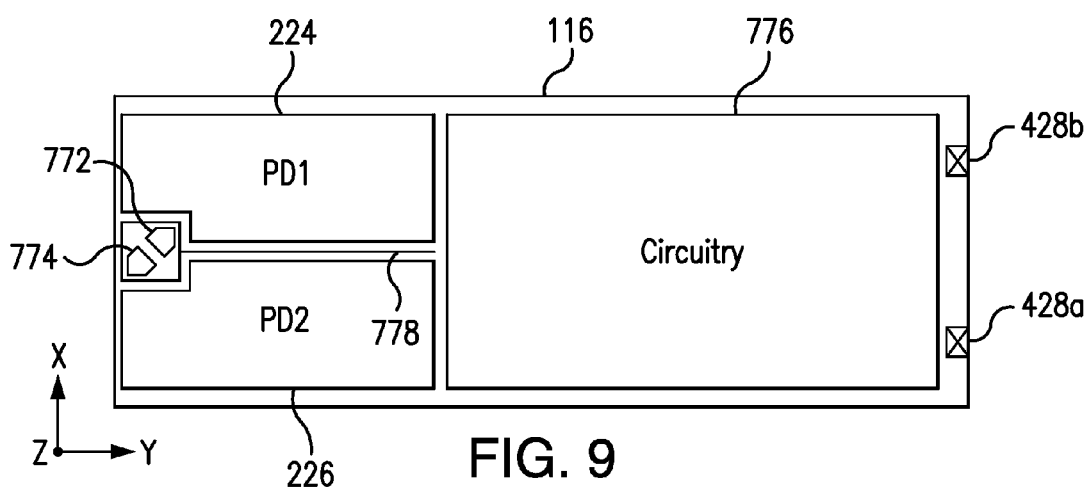

The layout of the first and second photodetectors 224 and 226 on silicon substrate 116 is not limited to the embodiment illustrated in FIG. 7. Other embodiments may use different photodetector layouts, such as, for example, those shown in FIGS. 8 and 9. FIG. 8 illustrates an embodiment of the silicon substrate 116 in which the photosensitive areas of the first and second photodetectors 224 and 226 do not extend all the way between the light source mounting pads 772 and 774. FIG. 9 illustrates an embodiment of the silicon substrate 116 in which the photosensitive areas of the first and second photodetectors 224 and 226 do not extend above and below the light source mounting pads 772 and 774.

Figure 10:
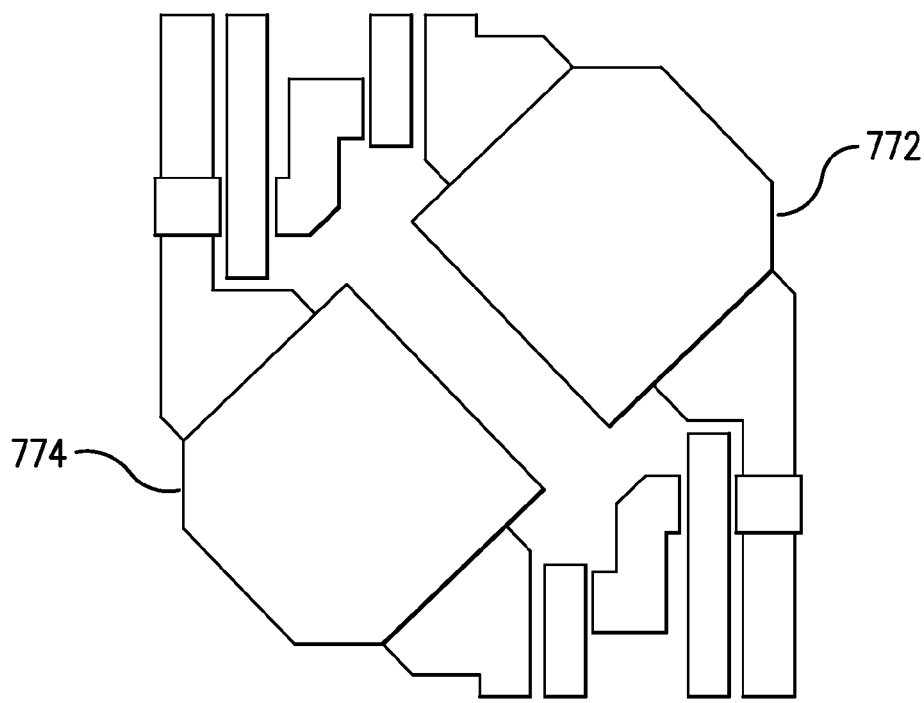
FIG. 10 illustrates the layout of light source mounting pads on a silicon substrate in accordance with an embodiment of the present invention.
Figure 11:
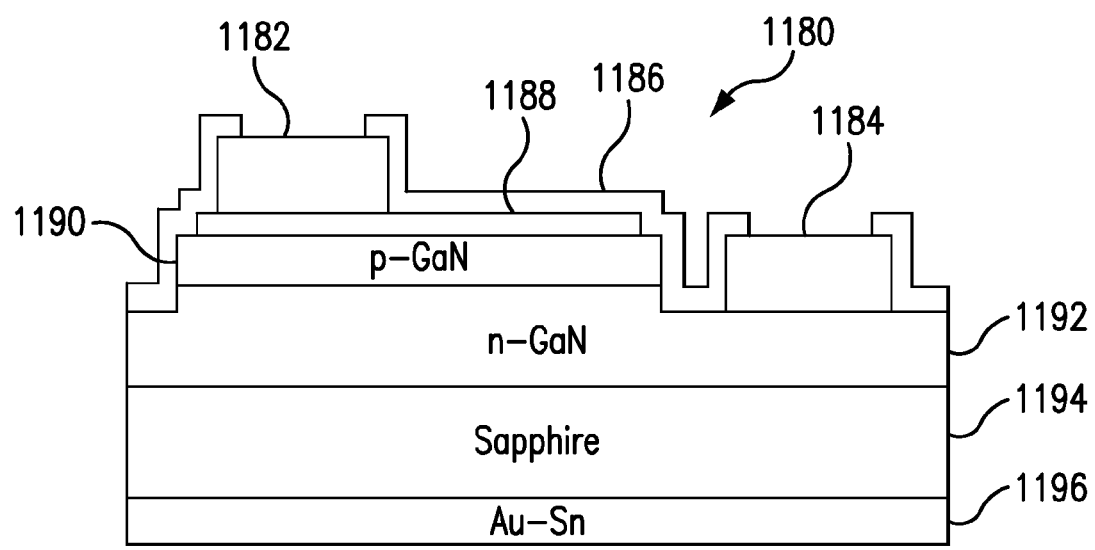
FIGS. 11 and 12 are a cross-sectional view and bottom view, respectively, of a flip-chip mounted light emitting diode that may be mounted to light source mounting pads on a silicon substrate in accordance with an embodiment of the present invention.
Figure 12:
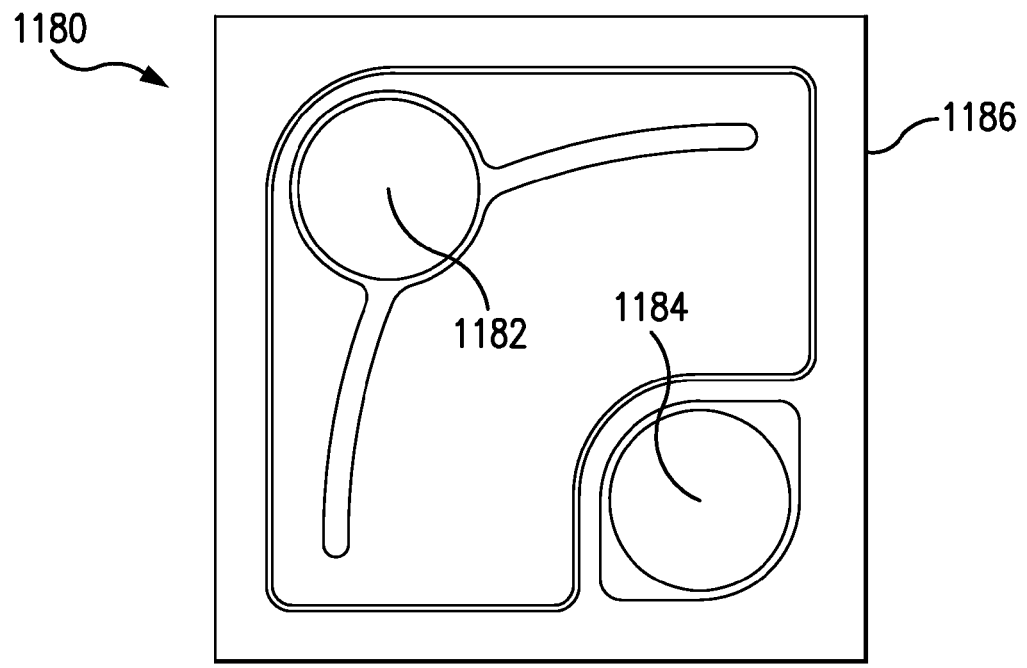

FIG. 10 illustrates the layout of the light source mounting pads 772 and 774 on silicon substrate 116 according to one embodiment of the silicon substrate 116. The light source mounting pads 772 and 774 may be flip-chip LED mounting pads configured for mounting of a flip-chip mounted LED, and light source 108 may be a flip-chip mounted LED, such as, for example, the flip-chip mounted LED 1180 illustrated in the cross-sectional view in FIG. 11. As shown in the FIG. 11, flip-chip mounted LED 1180 may have an anode 1182, a cathode 1184, a cover layer 1186, a transparent electrode 1188, a p-type semiconductor (e.g., Gallium Nitride (GaN)) layer 1190, an n-type semiconductor (e.g., GaN) layer 1192, a substrate (e.g., sapphire substrate) layer 1194 and/or a backside metal (e.g., a gold tin alloy (Au—Sn)) layer 1196. FIG. 12 is a bottom view of the flip-chip mounted LED 1180 shown in FIG. 11 and illustrates the anode 1182 and cathode 1184, which connect to light source mounting pads 772 and 774 when the flip-chip mounted LED 1180 is mounted on the silicon substrate 116.

Figure 13:
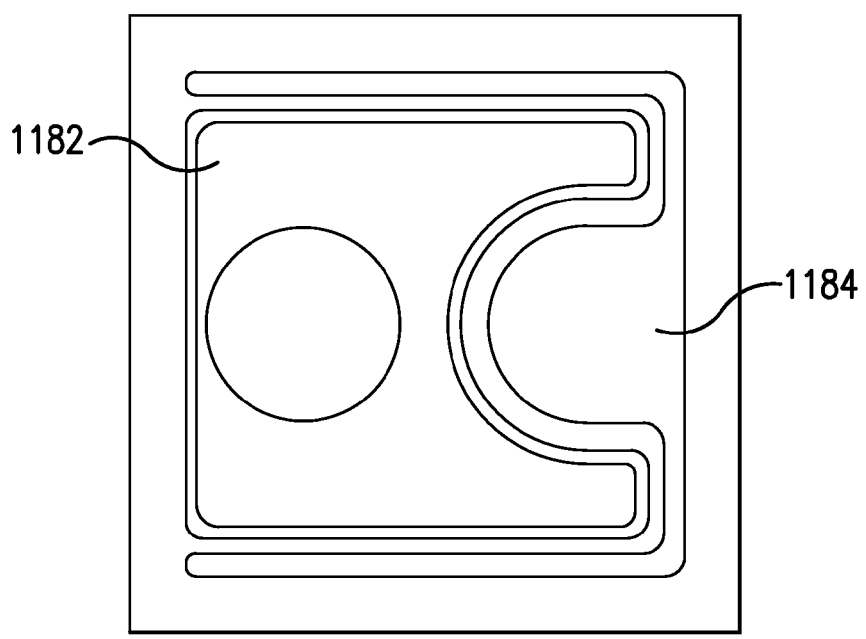
FIG. 13 illustrates the layout of light source mounting pads on a silicon substrate in accordance with an alternative embodiment of the present invention.

Although FIG. 10 illustrates the layout of the light source mounting pads 772 and 774 according to the one embodiment, other embodiments may use other layouts, including other flip-chip LED mounting pad layouts. For example, FIG. 13 illustrates the layout of the light source mounting pads 772 and 774 on silicon substrate 116 according to one possible alternative embodiment of the silicon substrate 116. Moreover, the silicon substrate 116 may be implemented with different light source mounting pad layouts for connecting to the different anode and cathode layouts of different light sources.

Figure 14:
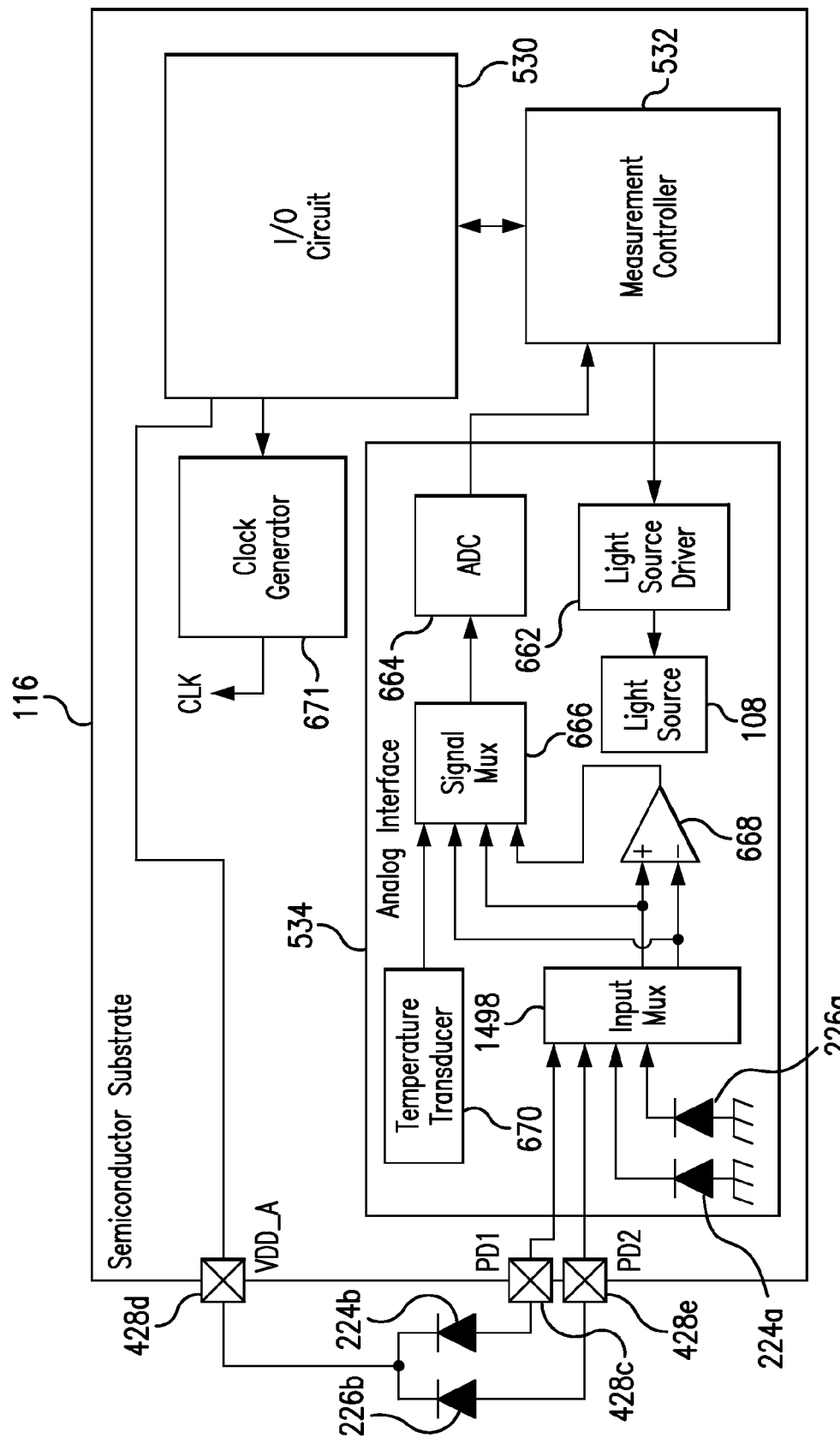
FIG. 14 illustrates the functional blocks of circuitry fabricated on a silicon substrate configured to support first and second internal photodetectors and first and second external photodetectors according to an exemplary embodiment of present invention.

In some embodiments, the silicon substrate 116 may be configured to support one or more internal photodetectors 110 (i.e., one or more photodetectors fabricated in the semiconductor substrate 116) and one or more external photodiodes 110. FIG. 14 illustrates an exemplary embodiment of the functional blocks of circuitry fabricated on a silicon substrate 116 configured to support first and second internal photodetectors 224a and 226a and first and second external photodetectors 224b and 226b. Relative to the embodiment illustrated in FIG. 6, the analog interface 534 of the embodiment of the functional blocks of circuitry fabricated on a silicon substrate 116 illustrated in FIG. 14 may additionally include an input multiplexor (MUX) 1498. The input MUX 1498 may selectively provide either the outputs of first and second internal photodetectors 224a and 226a or the outputs of the first and second external photodetectors 224b and 226b as outputs to the comparator 668 and/or signal MUX 666.

Figure 15:
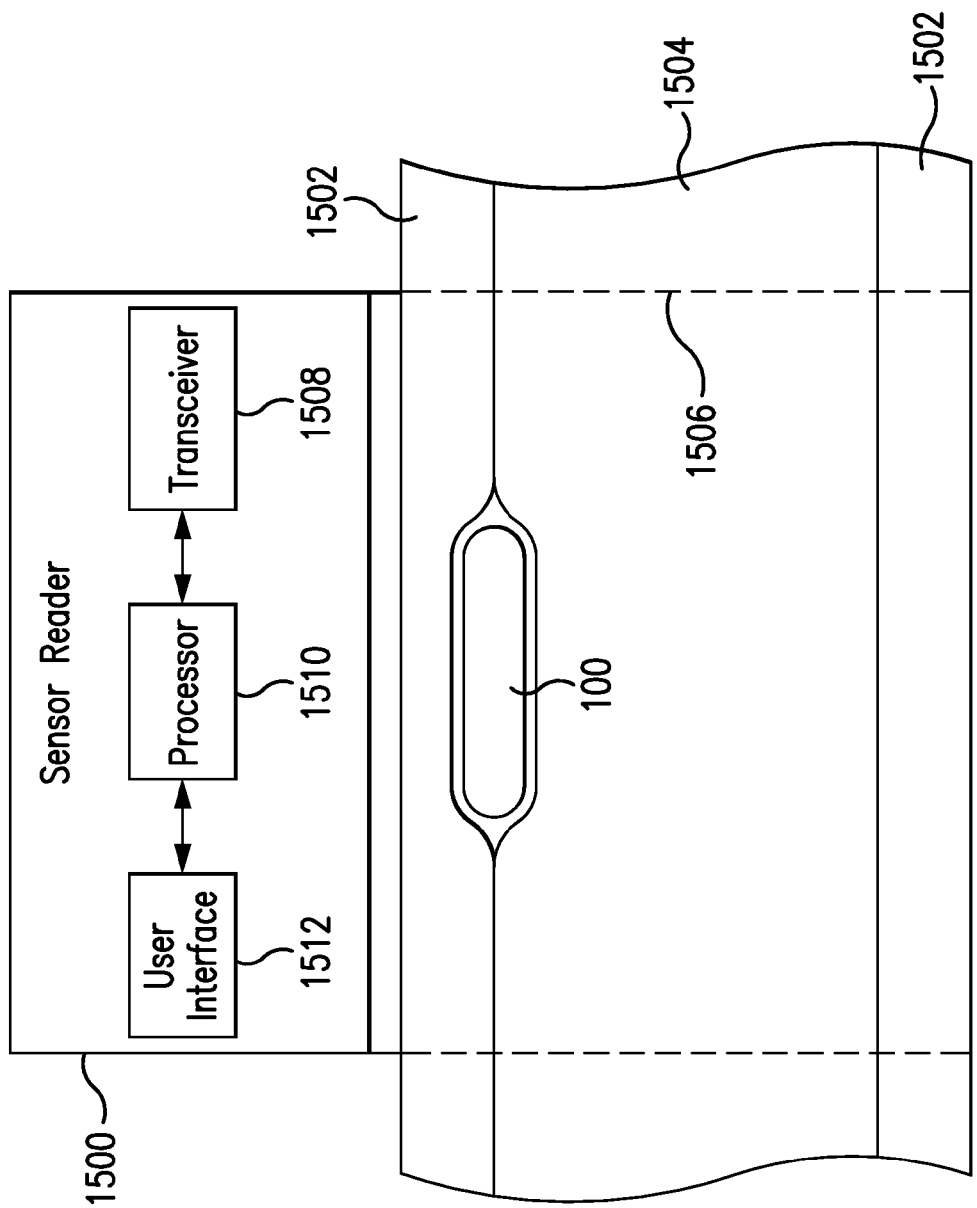
FIG. 15 illustrates an example of a sensor system, which includes an optical sensor and a sensor reader, embodying aspects of the present invention.

FIG. 15 illustrates an example of a sensor system including sensor 100 and a sensor reader 1500 according to one embodiment of the present invention. In the embodiment shown in FIG. 15, the sensor 100 may be implanted, for example, near a patient's wrist. For example, as shown in FIG. 15, in one non-limiting embodiment, the sensor 100 may be implanted between the skin 1502 and subcutaneous tissues 1504. In a non-limiting embodiment, the reader 1500 may be worn like a watch on the patient's arm. That is, the reader 1500 may be attached to a wristband 1506. In some embodiments, the reader 1500 may be combined with a conventional watch. In a non-limiting embodiment, the wristband 1506 is an opaque wristband that may reduce the amount of ambient light that reaches the implanted sensor 100. However, in other embodiments, the reader 1500 may not be worn or otherwise attached to the patient, and the patient may simply bring the sensor 100 into proximity of the reader 1500 by bringing the reader 1500 near the patient's wrist. Furthermore, in some embodiments, the sensor 100 may be implanted in a part of the patient's body other than near the patient's wrist, such as, for example, in the abdomen or an upper part of the arm.

In some embodiments, the sensor reader 1500 may include a transceiver 1508, a processor 1510 and/or a user interface 1512. In one embodiment, the user interface 1512 may include a liquid crystal display (LCD), but, in other embodiments, different types of displays may be used. In some embodiments, the transceiver 1508 may include an inductive element, such as, for example, a coil. The transceiver 1508 may generate an electromagnetic wave (e.g., by using a coil) to induce a current in the inductive element 114 of the sensor 100, which powers the sensor 100. The transceiver 1508 may also transmit data (e.g., commands) to the sensor 100. For example, in a non-limiting embodiment, the transceiver 1508 may transmit data by modulating the generated electromagnetic wave used to power the sensor 100 (e.g., by modulating the current flowing through a coil of the transceiver 1508). As described above, the modulation in the electromagnetic wave generated by the reader 1500 may be detected/extracted by the sensor 100 (e.g., by data extractor 642). Moreover, the transceiver 1508 may receive data (e.g., measurement information) from the sensor. For example, in a non-limiting embodiment, the transceiver 1508 may receive data by detecting modulations in the electromagnetic wave generated by the sensor 100 (e.g., by clamp/modulator 646), e.g., by detecting modulations in the current flowing through the coil of the transceiver 1508.

In some embodiments, the processor 1510 may output to the transceiver 1508 the data to be transmitted to the sensor 100 and may receive from the transceiver 1508 the data received from the sensor 100. In one embodiment, the processor 1510 may serialize and encode the data to be transmitted to the sensor 100 before outputting it to the transceiver 1508 for transmission. Similarly, the processor 1510 may decode and/or serialize the data received from the sensor 100. In some embodiments, the data received from the sensor 100 may be measurement information, and the processor 1510 may process the measurement information to determine a concentration of an analyte. However, in other embodiments, the sensor 100 may process the measurement information to determine a concentration of an analyte, and the data received from the sensor 100 may be the determined concentration of the analyte. In some embodiments, the processor 1510 may cause the user interface 1512 to display a value representing the concentration of the analyte so that a user (e.g., the patient, a doctor and/or others) can read the value. Also, in some embodiments, the processor 1510 may receive from the user interface 1512 user input (e.g., a user request for a sensor reading, such as the concentration of an analyte).

In some embodiments, the sensor reader 1500 may include one or more photodetectors. In one embodiment, the sensor reader 1500 may use the one or more photodetectors to detect ambient light, and, if to much light is detected, issue a warning to the user via user interface 1512. In some embodiments, the system including sensor reader 1500 and sensor 100 may incorporate the methods for ambient light detection and warning issuance described in U.S. Pat. No. 7,157,723, which is incorporated herein by reference in its entirety. Furthermore, in some embodiments, the sensor reader 1500 may include one or more input/output ports that enable transmission of data (e.g., traceability information and/or measurement information) and receipt of data (e.g., sensor commands and/or setup parameters) between the sensor reader 1500 and another device (e.g., a computer).

In some embodiments, such as, for example, those illustrated FIGS. 7-9, where the circuitry 776 and first and second photodetectors 224 and 226 may be fabricated in semiconductor substrate 116, the semiconductor substrate 116 may provide a custom integrated circuit that merges full functionality for an optical sensor interface onto a single chip that needs only minimal connections to external passive components (e.g., capacitors 118) and/or a light source 108 (e.g., LED). In fact, in some embodiments, the number of external components of sensor 100 connected to the circuitry fabricated the semiconductor substrate 116 may be reduced to five or fewer (e.g., one or more capacitors 118, inductive element 114 and/or light source 108). Furthermore, in some embodiments, the light source 108 may also be fabricated in the semiconductor substrate 116. The reduced external component count and associated reduction in the number of connections may contribute to improved sensor robustness and/or to reduce manufacturing complexity.

According to aspects of the present invention, the circuitry fabricated in semiconductor substrate 116, which may include one or more photodetectors 110 and/or light source 108, may provide an optical transduction along with the ability to receive and transmit data through a remotely powered, wireless interface. In other words, the functionality of sensor 100 may include remote powering and bi-directional wireless data communication. The circuitry fabricated in semiconductor substrate 116 may have the ability to check the received power through its remotely powered interface as well as check that the regulated voltages are sufficient to supply power to all of the blocks.

As explained above, in some embodiments of the present invention, the circuitry fabricated in semiconductor substrate 116 may also have the ability to execute diagnostic measurements that check the integrity of various blocks (e.g., comparator 668 and/or ADC 664) in the analog front end (e.g., analog interface 534) of the chip. The one or more photodetectors 110 may provide the light to current transduction, which may be processed further through the integrated comparator (e.g., transimpedance amplifier) 668 and ADC 664. The analog interface 534 may also have a temperature transducer 670, which, in some embodiments, may be an integrated, band-gap based temperature sensor. In some embodiments, the temperature transducer 670 may provide temperature as an independent measurement and/or for optical or system compensation since (e.g., in one embodiment) the output of the temperature transducer 670 may be processed along with the fluorescence information received through the one or more photodetectors 110.

In some embodiments, the analog interface 534, acting under the control of the measurement controller 532, may execute a measurement sequence (e.g., measurement command execution process 1700, which is described below with reference to FIGS. 17 and 18) and then report the results to the sensor reader 1500. In one embodiment, the measurement sequence may be a pre-loaded sequence (i.e., a pre-stored timing sequence). In some embodiments, the measurement sequence may have multiple time slots for one or more measurements from first photodetector 224, one or more measurements from second photodetector 226, one or more difference measurements comparing the currents from first and second photodetectors 224 and 226, one or more temperature measurements of the silicon substrate 116 and/or sensor 100, one or more field current measurements (i.e., measurements of the incident power received through the inductive element 114), one or more excitation current source regulation measurements (i.e., measurements to check that the light source 108 is in regulation), one or more voltage measurements and/or one or more diagnostic measurements to ensure proper functionality of the various component blocks of the analog interface 543. In various embodiments, the sensor 100 may be used for continuous readout and/or power up on demand for a remotely queried measurement.

In some embodiments, each of these measurements may be digitized through ADC 664, which may also be fabricated in the semiconductor substrate 116. Because the ADC 664 may convert one or more analog measurements to digital measurements, in some embodiments, the bi-directional wireless data communication may be bi-directional, digital wireless data communication. Digital data communication may have an improved signal integrity relative to analog data communication, and, in some embodiments, the sensor 100 may utilize solely digital data communication as opposed analog data communication. In a non-limiting embodiment, all or a portion of the data is transmitted according to a known protocol that includes a checksum.

Figure 16:
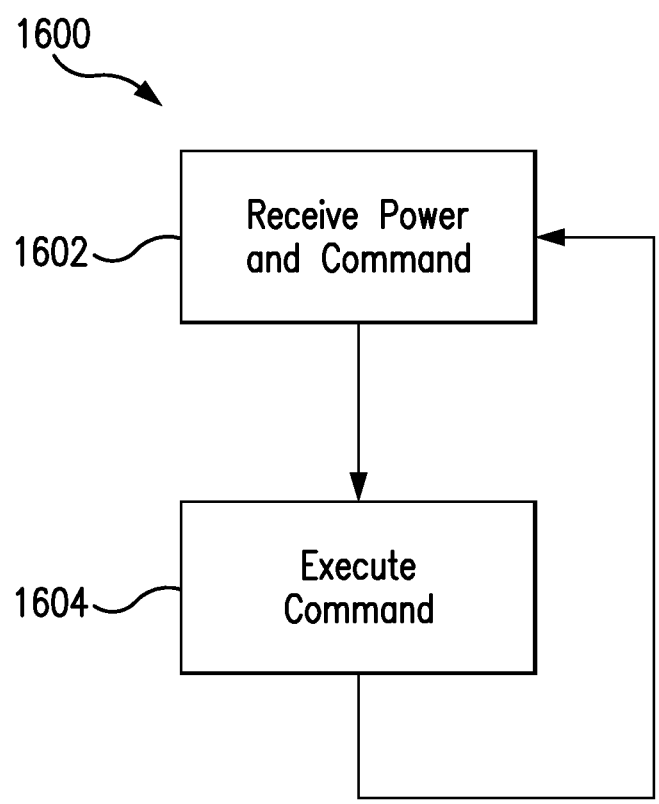
FIG. 16 illustrates a sensor control process that may be performed by the optical sensor in accordance with an embodiment of the present invention.

FIG. 16 illustrates an exemplary sensor control process 1600 that may be performed by the optical sensor 100, which may be, for example, implanted within a living animal (e.g., a living human), in accordance with an embodiment of the present invention. The sensor control process 1600 may begin with a step 1602 of wirelessly receiving one or more commands and power. In one embodiment, the power may be in the form of a modulated electromagnetic wave the sensor 100 may receive. The modulated electromagnetic wave may induce a current in inductive element 114, and the input/output circuit 530 may convert the induced current into power for operating the sensor 100 and extract and decode commands from the induced current. In a non-limiting embodiment, rectifier 640 may be used to convert the induced current into operating power for the sensor 100, data extractor 642 may extract data from the current induced in inductive element 114, decoder/serializer 650 may decode and serialize the extracted data, and command decoder/data encoder 652 may decode one or more commands from the decoded and serialized extracted data. The one or more decoded commands may then be sent to measurement controller 532 via the data and control bus 654. In some embodiments, the one or more commands and power received by the sensor 100 may be transmitted by the transceiver 1508 of sensor reader 1500.

In step 1604, the optical sensor 100 may execute the received command. For example, in one embodiment, the optical sensor 100 may execute the received command under control of the measurement controller 532. Example command execution processes that may be performed by the optical sensor 100 in step 1602 to execute the received commands are described below with reference to FIGS. 17-20.

Examples of commands that may be received and executed by the sensor 100 may include measurement commands, get result commands and/or get traceability information commands. Examples of measurement commands may include measure sequence commands (i.e., commands to perform a sequence of measurements, and after finishing the sequence, transmitting the resulting measurement information), measure and save commands (i.e., commands to perform a sequence of measurements and, after finishing the sequence, saving the resulting measurement information without transmitting the resulting measurement information) and/or single measurement commands (i.e., commands to perform a single measurement). The single measurement commands may be commands to save and/or transmit the measurement information resulting from the single measurement. The measurement commands may or may not include setup parameters (i.e., calibration information). Measurement commands that do not have setup parameters may, for example, be executed using stored setup parameters (e.g., in nonvolatile storage medium 660). Other measurement commands, such as measurement commands to both save and transmit the resulting measurement information, are possible. The commands that may be received and executed by the sensor 100 may also include commands to update the stored the setup parameters. The examples of commands described above are not exhaustive of all commands that may be received and executed by the sensor 100, which may be capable of receiving and executing one or more of the commands listed above and/or one or more other commands.

Figure 17:
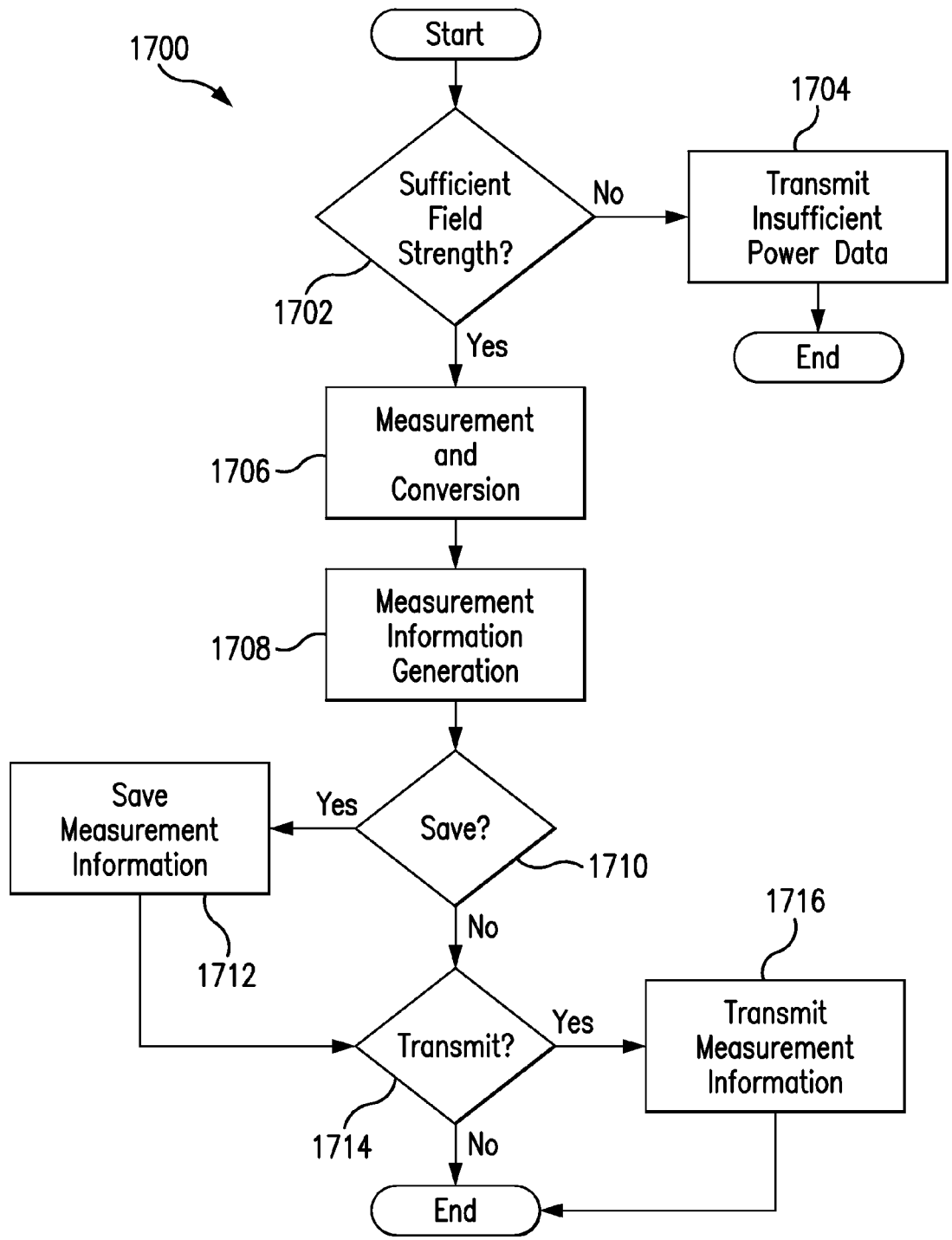
FIG. 17 illustrates a measurement command execution process that may be performed by the optical sensor to execute a measurement command received by the optical sensor in accordance with an embodiment of the present invention.

FIG. 17 illustrates a measurement command execution process 1700 that may be performed in step 1604 of the sensor control process 1600 by the optical sensor 100 to execute a measurement command received by the optical sensor 100 in accordance with an embodiment of the present invention. The measurement command execution process 1700 may begin with a step 1702 of determining whether the wirelessly received power is sufficient to execute the received measurement command. In other words, in step 1702, the sensor 100 may determine whether the electromagnetic field or wave that may induce a current in inductive element 114 is strong enough to generate sufficient operating power for execution of the received measurement command, which, as described below, may include using light source 108 to irradiate indicator molecules 104. In one embodiment, step 1702 may be performed by a field strength measurement circuit, which may be part of the measurement controller 532 or may be a separate component of the circuitry 776 on the silicon substrate 116.

In some embodiments, if the sensor 100 determines in step 1702 that the wirelessly received power is insufficient to execute the received measurement command, the measurement command execution process 1700 may proceed to a step 1704 in which the sensor 100 may transmit (e.g., by way of the input/output circuit 530 and inductive element 114) data indicating that that the wirelessly received power is insufficient to execute the received measurement command. In some embodiments, the insufficient power data may merely indicate that the power is insufficient, but in other embodiments, the insufficient power data may indicate the percentage of the power needed to execute the received measurement command that is currently being received.

In one embodiment, upon detection that the received power is insufficient, the measurement controller 532 may output insufficient power data to the data and control bus 654. The data and control bus 654 may transfer the insufficient power data to the command decoder/data encoder 652, which may encode the insufficient power data. The data serializer 656 may serialize the encoded insufficient power data. The encoder 658 may encode the serialized insufficient power data. The clamp/modulator 646 may modulate the current flowing through the inductive element 114 (e.g., coil 220) as a function of the encoded insufficient power data. In this way, the encoded insufficient power data may be transmitted wirelessly by the inductive element 114 as a modulated electromagnetic wave. In some embodiments, the encoded insufficient power data wirelessly transmitted by the sensor 100 may be received by the sensor reader 1500, which may display a message on user interface 1512 a message indicating that the power received by the sensor 100 is insufficient and/or the extent to which the received power is insufficient.

In some embodiments, if the sensor 100 determines in step 1702 that the wirelessly received power is sufficient to execute the received measurement command, the measurement command execution process 1700 may proceed to a step 1706 in which a measurement and conversion process may be performed. The measurement and conversion process may, for example, be performed by the analog interface 534 under control of the measurement controller 532. In one embodiment, the measurement and conversion sequence may include generating one or more analog measurements (e.g., using one or more of temperature transducer 670, light source 108, first photodetector 224, second photodetecor 226 and/or comparator 668) and converting the one or more analog measurements to one or more digital measurements (e.g., using ADC 664). One example of the measurement conversion process that may be performed in step 1706 is described in further detail below with reference to FIG. 18.

At step 1708, the optical sensor 100 may generate measurement information in accordance with the one or more digital measurements produced during the measurement and conversion sequence performed in step 1706. Depending on the one or more digital measurements produced in step 1706, the measurement information may be indicative of the presence and/or concentration of an analyte in a medium in which the sensor 100 is implanted. In one embodiment, in step 1706, the measurement controller 532 may receive the one or more digital measurements and generate the measurement information.

At step 1710, the optical sensor 100 may determine whether the measurement information generated in step 1708 should be saved. In some embodiments, the measurement controller 532 may determine whether the measurement information should be saved. In one embodiment, the measurement controller 532 may determine whether the measurement information should be saved based on the received measurement command. For example, if the measurement command is a measure and save command or other measurement command that includes saving the resulting measurement information, the measurement controller 532 may determine that the measurement information generated in step 1708 should be saved. Otherwise, if the measurement command is a measure sequence command or other measurement command that does not include saving the resulting measurement information, the measurement controller 532 may determine that the measurement information generated in step 1708 should not be saved.

In some embodiments, if the sensor 100 determines in step 1710 that the measurement information generated in step 1708 should be saved, the measurement command execution process 1700 may proceed to a step 1712 in which the sensor 100 may save the measurement information. In one embodiment, after determining that the measurement information generated in step 1708 should be saved, the measurement controller 532 may output the measurement information to the data and control bus 654, which may transfer the measurement information to the nonvolatile storage medium 660. The nonvolatile storage medium 660 may save the received measurement information. In some embodiments, the measurement controller 532 may output, along with the measurement information, an address at which the measurement information is to be saved in the nonvolatile storage medium 660. In some embodiments, the nonvolatile storage medium 660 may be configured as a first-in-first-out (FIFO) or last-in-first-out (LIFO) memory.

In some embodiments, if the sensor 100 determines in step 1710 that the measurement information generated in step 1708 should not be saved, or after saving the measurement information in step 1712, the measurement command execution process 1700 may proceed to a step 1714 in which the optical sensor 100 may determine whether the measurement information generated in step 1708 should be transmitted. In some embodiments, the measurement controller 532 may determine whether the measurement information should be transmitted. In one embodiment, the measurement controller 532 may determine whether the measurement information should be transmitted based on the received measurement command. For example, if the measurement command is a measure sequence command or other measurement command that includes transmitting the resulting measurement information, the measurement controller 532 may determine that the measurement information generated in step 1708 should be transmitted. Otherwise, if the measurement command is a measure and save command or other measurement command that does not include transmitting the resulting measurement information, the measurement controller 532 may determine that the measurement information generated in step 1708 should not be transmitted.

In some embodiments, if the sensor 100 determines in step 1714 that the measurement information generated in step 1708 should be transmitted, the measurement command execution process 1700 may proceed to a step 1716 in which the sensor 100 may transmit the measurement information. In one embodiment, after determining that the measurement information generated in step 1708 should be transmitted, the measurement controller 532 may output the measurement information to the data and control bus 654. The data and control bus 654 may transfer the measurement information to the command decoder/data encoder 652, which may encode the measurement information. The data serializer 656 may serialize the encoded measurement information. The encoder 658 may encode the serialized measurement information. The clamp/modulator 646 may modulate the current flowing through the inductive element 114 (e.g., coil 220) as a function of the encoded measurement information. In this way, the encoded measurement information may be transmitted wirelessly by the inductive element 114 as a modulated electromagnetic wave. In some embodiments, the encoded measurement information wirelessly transmitted by the sensor 100 may be received by the sensor reader 1500, which may display a value representing the concentration of the analyte so that a user (e.g., the patient, a doctor and/or others) can read the value.

In some embodiments, after the sensor 100 (a) transmitted insufficient power data in step 1704, (b) determined in step 1714 that the measurement information generated in step 1708 should not be transmitted or (c) transmitted measurement information in step 1716, the measurement command execution process 1700 that may be performed in step 1604 of the sensor control process 1600 by the optical sensor 100 to execute a measurement command received by the optical sensor 100 may be completed, and, at this time, the sensor control process 1600 may return to step 1602.

Figure 18:
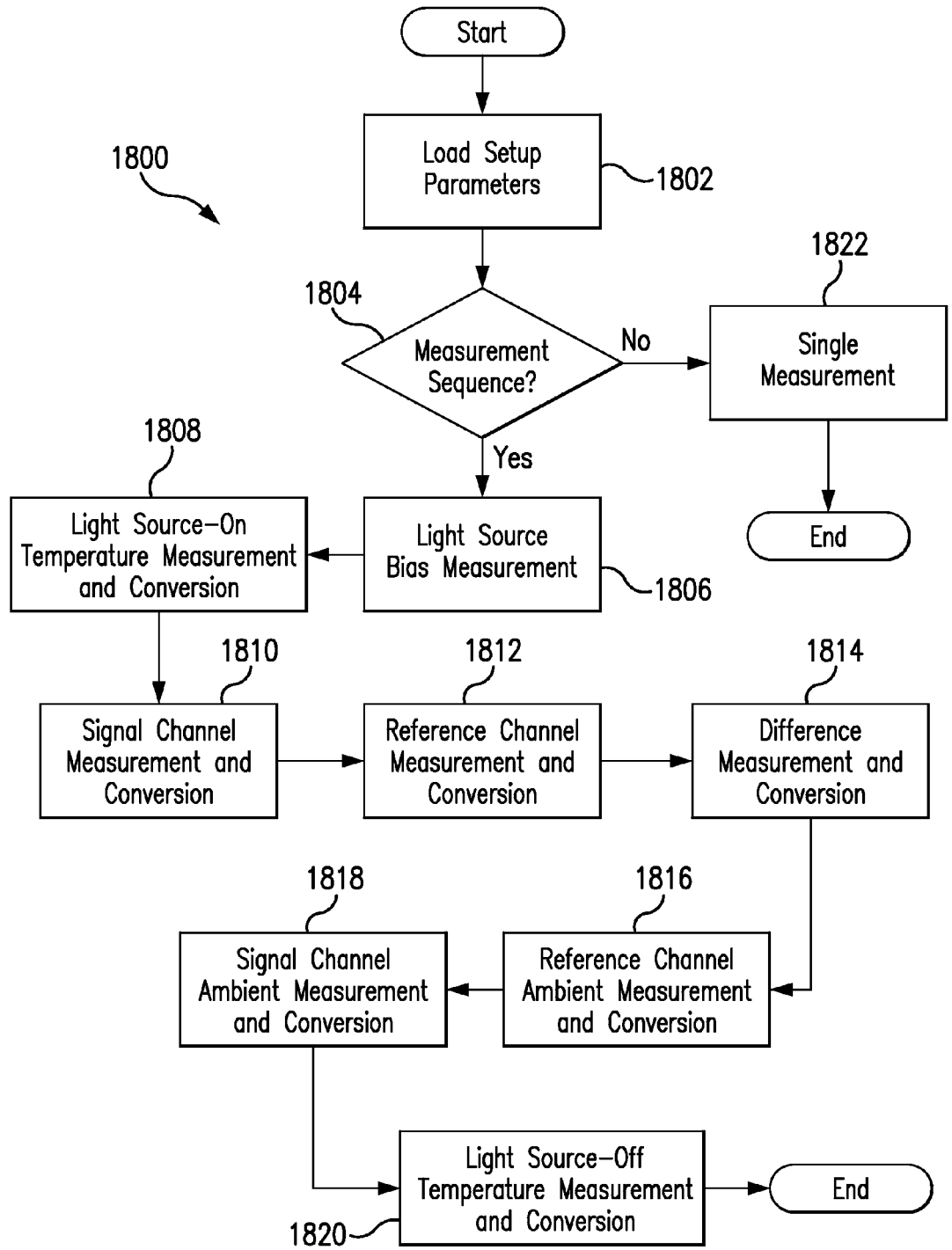
FIG. 18 illustrates a measurement and conversion process that may be performed in a step of the measurement command execution process, in accordance with an embodiment of the present invention.

FIG. 18 illustrates a measurement and conversion process 1800, which is an example of the measurement and conversion process that may be performed in step 1706 of the measurement command execution process 1700, in accordance with an embodiment of the present invention.

At step 1802, the sensor 100 may load setup parameters (i.e., calibration information) for performing one or more measurements in accordance with the received measurement command. For example, in one embodiment, the measurement controller 532 may load one or more setup parameters by setting up one or more components (e.g., light source 108, first photodetector 224, second photodetector 226, comparator 668 and/or temperature transducer 534) of the analog interface 534 with the setup parameters. In some embodiments, the nonvolatile storage medium 660 may store saved setup parameters. Further, as noted above, in some embodiments, the measurement commands may or may not include setup parameters. In a non-limiting embodiment, if the measurement command includes one or more setup parameters, the measurement controller 532 may setup one or more components of the analog interface 534 with the setup parameters with the one or more setup parameters included in the measurement command. However, if the measurement command does not include one or more setup parameters, the measurement controller 532 may obtain saved setup parameters stored in the nonvolatile storage medium 660 and setup one or more components of the analog interface 534 with the saved setup parameters obtained from the nonvolatile storage medium 660.

At step 1804, the sensor 100 may determine whether to execute a single measurement or a measurement sequence. In some embodiments, the measurement controller 532 may make the single measurement vs. measurement sequence determination by referring to the received measurement command (i.e., is the measurement command to execute a single measurement or to execute a measurement sequence?). For example, in some embodiments, if the measurement command is a measure sequence command, a measure and save command or other command for a measurement sequence, the measurement controller 532 may determine that a measurement sequence should be executed. However, if the measurement command is a single measurement command, the measurement controller 532 may determine that a single measurement should be executed.

In some embodiments, if the sensor 100 determines in step 1804 that a measurement sequence should be performed, the sensor 100 may perform measurement and conversion sequence steps 1806-1820 of measurement and conversion process 1800. However, in other embodiments, the sensor 100 may perform a portion of measurement and conversion sequence steps 1806-1820 and/or additional measurement and conversion sequence steps.

At step 1806, the sensor 100 may perform a light source bias measurement and conversion. For example, in some embodiments, while the light source 108 is on (i.e., while the light source 108, under the control of the measurement controller 532, is emitting excitation light and irradiating indicator molecules 104), the analog interface 534 may generate an analog light source bias measurement signal. In one embodiment, the ADC 664 may convert the analog light source bias measurement signal to a digital light source bias measurement signal. The measurement controller 532 may receive the digital light source bias measurement signal and generate (e.g., in step 1708 of the measurement command execution process 1700) the measurement information in accordance with the received digital light source bias measurement signal. In a non-limiting embodiment, the analog interface 534 may generate the analog light source bias measurement signal by sampling the voltage and the current in the output of the current source that feeds the light source 108.

At step 1808, the sensor 100 may perform a light source-on temperature measurement and conversion. For example, in some embodiments, while the light source 108 is on (i.e., while the light source 108, under the control of the measurement controller 532, is emitting excitation light and irradiating indicator molecules 104), the analog interface 534 may generate a first analog temperature measurement signal indicative of a temperature of the sensor 100. In one embodiment, the temperature transducer 670 may generate the first analog temperature measurement signal while the light source 108 is on. The ADC 664 may convert the first analog temperature measurement signal to a first digital temperature measurement signal. The measurement controller 532 may receive the first digital temperature measurement signal and generate (e.g., in step 1708 of the measurement command execution process 1700) the measurement information in accordance with the received first digital temperature measurement signal.

At step 1810, the sensor 100 may perform a first photodetector measurement and conversion. For example, in some embodiments, while the light source 108 is on (i.e., while the light source 108, under the control of the measurement controller 532, is emitting excitation light and irradiating indicator molecules 104), the first photodetector 224 may generate a first analog light measurement signal indicative of the amount of light received by the first photodetector 224 and output the first analog light measurement signal to the signal MUX 666. The signal MUX 666 may select the first analog light measurement signal and, the ADC 664 may convert the first analog light measurement signal to a first digital light measurement signal. The measurement controller 532 may receive the first digital light measurement signal and generate (e.g., in step 1708 of the measurement command execution process 1700) the measurement information in accordance with the received first digital light measurement signal.

In a non-limiting embodiment, first photodetector 224 may be a part of a signal channel, the light received by the first photodetector 224 may be emitted by indicator molecules 104 distributed throughout the indicator membrane 106', and the first analog light measurement signal may be an indicator measurement.

At step 1812, the sensor 100 may perform a second photodetector measurement and conversion. For example, in some embodiments, while the light source 108 is on (i.e., while the light source 108, under the control of the measurement controller 532 is emitting excitation light and irradiating indicator molecules 104), the second photodetector 226 may generate a second analog light measurement signal indicative of the amount of light received by the second photodetector 226 and output the second analog light measurement signal to the signal MUX 666. The signal MUX 666 may select the second analog light measurement signal and, the ADC 664 may convert the second analog light measurement signal to a second digital light measurement signal. The measurement controller 532 may receive the second digital light measurement signal and generate (e.g., in step 1708 of the measurement command execution process 1700) the measurement information in accordance with the received second digital light measurement signal.

In a non-limiting embodiment, second photodetector 226 may be a part of a reference channel, the light received by the second photodetector 226 may be emitted by indicator molecules 104 distributed throughout the reference membrane 106", and the second analog light measurement signal may be a reference measurement.

At step 1814, the sensor 100 may perform a difference measurement and conversion. For example, in some embodiments, while the light source 108 is on (i.e., while the light source 108, under the control of the measurement controller 532, is emitting excitation light and irradiating indicator molecules 104), (i) the first photodetector 224 may generate a first analog light measurement signal indicative of the amount of light received by the first photodetector 224, and (ii) the second photodetector 226 may generate a second analog light measurement signal indicative of the amount of light received by the second photodetector 226. The comparator 668 may receive the first and second analog light measurement signals and generate an analog light difference measurement signal indicative of a difference between the first and second analog light measurement signals. The comparator 668 may output the analog light difference measurement signal to the signal MUX 666. The signal MUX 666 may select the analog light difference measurement signal and, the ADC 664 may convert the analog light difference measurement signal to a digital light difference measurement signal. The measurement controller 532 may receive the digital light difference measurement signal and generate (e.g., in step 1708 of the measurement command execution process 1700) the measurement information in accordance with the received digital light difference measurement signal.

In a non-limiting embodiment, first photodetector 224 may be a part of a signal channel, second photodetector 226 may be a part of a reference channel, and the analog light difference measurement signal may be indicative of the difference in light emitted by (a) indicator molecules 104 distributed throughout indicator membrane 106' and affected by the concentration of an analyte in the medium in which sensor 100 is implanted, and (b) indicator molecules 104 distributed throughout reference membrane 106" and unaffected by the concentration of the analyte in the medium in which sensor 100 is implanted.

At step 1816, the sensor 100 may perform a second photodetector ambient measurement and conversion. For example, in some embodiments, while the light source 108 is off (i.e., while the light source 108, under the control of the measurement controller 532 is not emitting light), the second photodetector 226 may generate a second analog ambient light measurement signal indicative of the amount of light received by the second photodetector 226 and output the second analog ambient light measurement signal to the signal MUX 666. The signal MUX 666 may select the second analog ambient light measurement signal and, the ADC 664 may convert the second analog ambient light measurement signal to a second digital ambient light measurement signal. The measurement controller 532 may receive the second digital ambient light measurement signal and generate (e.g., in step 1708 of the measurement command execution process 1700) the measurement information in accordance with the received second digital ambient light measurement signal.

In a non-limiting embodiment, second photodetector 226 may be a part of a reference channel, the light received by the second photodetector 226 may be emitted by indicator molecules 104 distributed throughout the reference membrane 106", and the second analog ambient light measurement signal may be an ambient reference measurement.

At step 1818, the sensor 100 may perform a first photodetector ambient measurement and conversion. For example, in some embodiments, while the light source 108 is off (i.e., while the light source 108, under the control of the measurement controller 532, is not emitting light), the first photodetector 224 may generate a first analog ambient light measurement signal indicative of the amount of light received by the first photodetector 224 and output the first analog ambient light measurement signal to the signal MUX 666. The signal MUX 666 may select the first analog ambient light measurement signal and, the ADC 664 may convert the first analog ambient light measurement signal to a first digital ambient light measurement signal. The measurement controller 532 may receive the first digital ambient light measurement signal and generate (e.g., in step 1708 of the measurement command execution process 1700) the measurement information in accordance with the received first digital ambient light measurement signal.

In a non-limiting embodiment, first photodetector 224 may be a part of a signal channel, the light received by the first photodetector 224 may be emitted by indicator molecules 104 distributed throughout the indicator membrane 106', and the first analog ambient light measurement signal may be an ambient indicator measurement.

At step 1820, the sensor 100 may perform a light source-off temperature measurement and conversion. For example, in some embodiments, while the light source 108 is off (i.e., while the light source 108, under the control of the measurement controller 532, is not emitting light), the analog interface 534 may generate a second analog temperature measurement signal indicative of a temperature of the sensor 100. In one embodiment, the temperature transducer 670 may generate the second analog temperature measurement signal while the light source 108 is off. The ADC 664 may convert the second analog temperature measurement signal to a second digital temperature measurement signal. The measurement controller 532 may receive the second digital temperature measurement signal and generate (e.g., in step 1708 of the measurement command execution process 1700) the measurement information in accordance with the received second digital temperature measurement signal.

Accordingly, in an embodiment in which sequence steps 1806-1820 of measurement and conversion process 1800 are performed, the measurement controller 532 may generate measurement information in accordance with (i) the first digital temperature measurement signal, (ii) the first digital light measurement signal, (iii) the second digital light measurement signal, (iv) the digital light difference measurement signal, (v) the second digital temperature measurement signal, (vi) the first digital ambient light measurement signal and (vii) the second digital ambient light measurement signal. In a non-limiting embodiment, the calculation of the concentration of the analyte performed by the measurement controller 532 of sensor 100 and/or sensor reader 1500 may include subtracting the digital ambient light signals from the corresponding digital light measurement signals. The calculation of the concentration of the analyte may also include error detection. In some embodiments, the measurement controller 532 may incorporate methods for attenuating the effects of ambient light, such as, for example, those described in U.S. Pat. No. 7,227,156, which is incorporated herein by reference in its entirety. In some embodiments, the measurement controller 532 may generate measurement information that merely comprises the digital measurement signals received from the analog interface 534. However, in other embodiments, the measurement controller 532 may process the digital signals received from the analog interface 534 and determine (i.e., calculate and/or estimate) the concentration of an analyte in the medium in which the sensor 100 is implanted, and the measurement information may, additionally or alternatively, include the determined concentration.

In some embodiments, if the sensor 100 determines in step 1804 that a measurement sequence should be performed, the measurement and conversion process 1800 may proceed to a step 1822 in which a single measurement and conversion is performed. In some embodiments, based on the measurement command received, the single measurement and conversion performed in step 1822 may be any one of the measurements and conversions performed in steps 1806-1820. Accordingly, in an example where step 1822 of the measurement and conversion process 1800 is performed, the measurement controller 532 may receive only one digital measurement signal, and the measurement information generated by the measurement controller 532 (e.g., in step 1708 of the measurement command execution process 1700) may, in one embodiment, simply be the one digital measurement signal received by the measurement controller.

In some embodiments, light source 108 may be turned on before execution of step 1806 and not turned off until after execution of step 1814. However, this is not required. For example, in other embodiments, the light source 108 may be turned on during measurement portions of steps 1806-1814 and turned off during the conversion portions of steps 1806-1814.

Furthermore, although FIG. 18 illustrates one possible sequence of the measurement and conversion process 1800, it is not necessary that steps 1806-1820 of the measurement and conversion process 1800 be performed in any particular sequence. For example, in one alternative embodiment, light measurement and conversion steps 1806-1814 may be performed in a different order (e.g., 1808, 1812, 1814, 1810, 1806), and/or ambient light measurement and conversion steps 1816-1820 may be performed in a different order (e.g., 1818, 1820, 1816). In some embodiments, the light source on temperature measurement may be used to provide an error flag in each individual measurement (e.g., by using a comparator to comparing the light source on temperature measurement to threshold value). In another alternative embodiment, ambient light measurement and conversion steps 1816-1820 may be performed before light measurement and conversion steps 1806-1814. In still another alternative embodiment, steps 1806-1820 of the measurement and conversion process 1800 may be performed in a sequence in which all of the steps of one of light measurement and conversion steps 1806-1814 and ambient light measurement and conversion steps 1816-1820 are completed before one or more steps of the other are executed (e.g., in one embodiment, steps 1806-1820 may be performed in the sequence 1806, 1808, 1810, 1818, 1816, 1812, 1814, 1820).

Figure 21A:
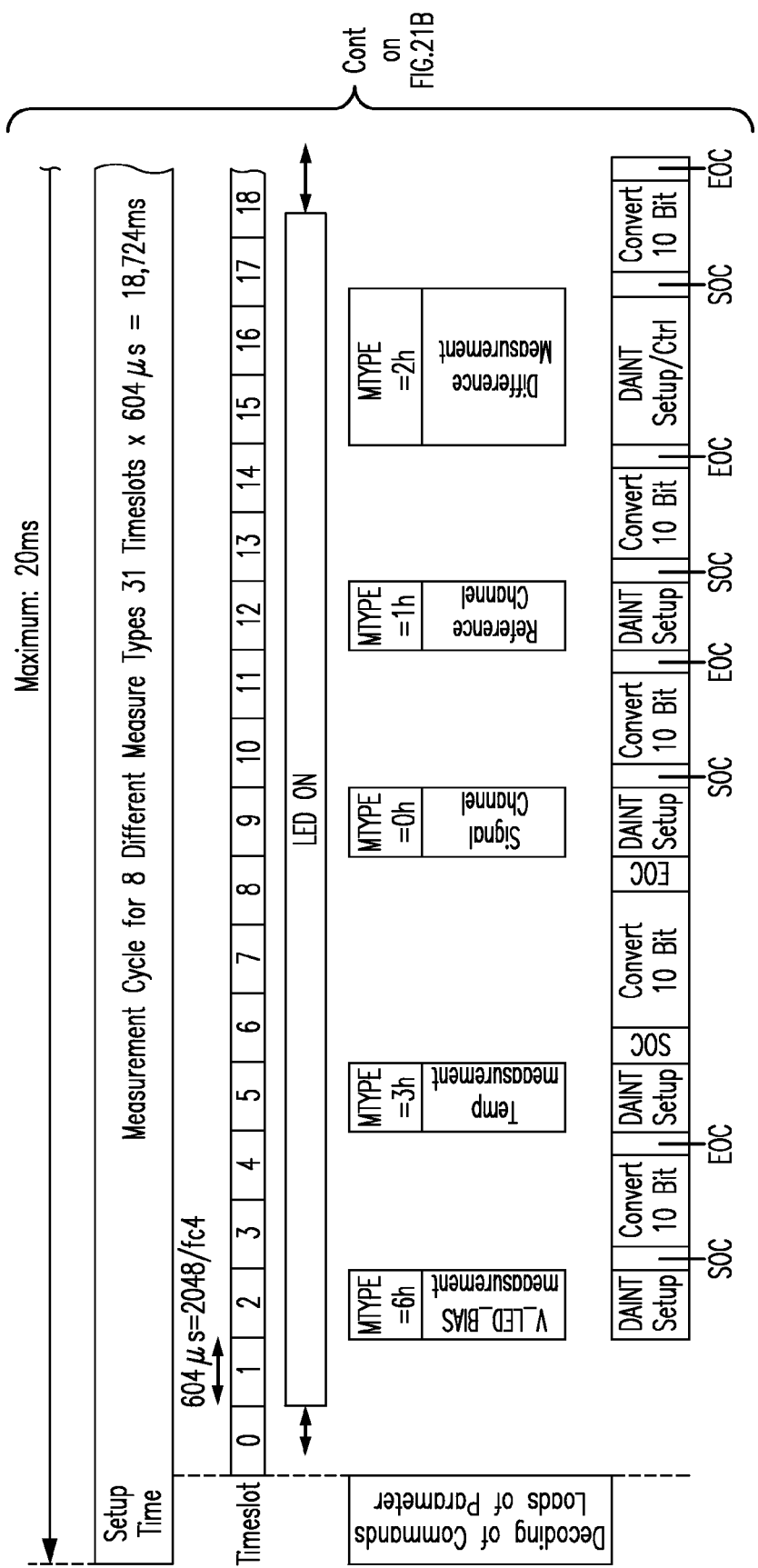
FIGS. 21A and 21B illustrate the timing of an exemplary embodiment of a measurement and conversion process in accordance with an embodiment of the present invention.
Figure 21B:
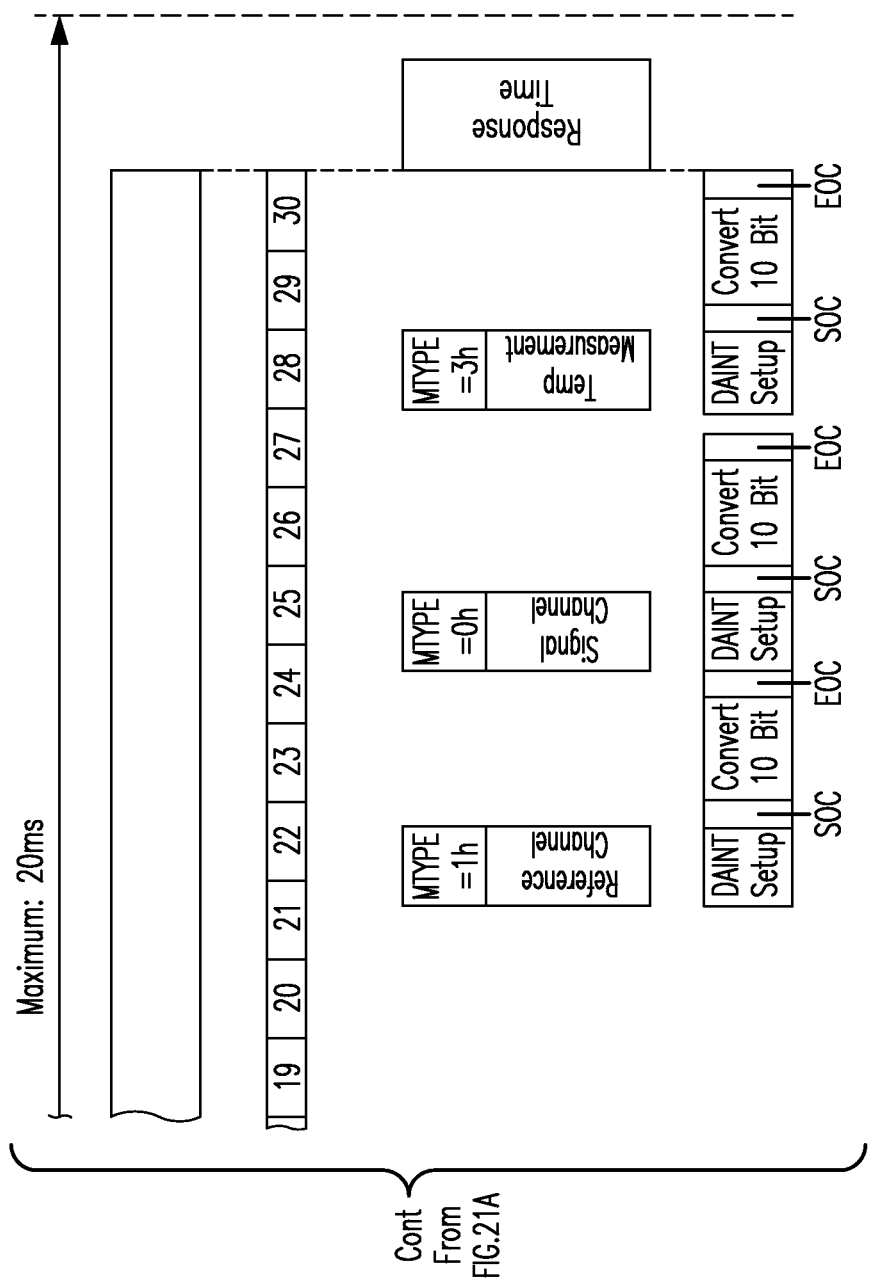

FIGS. 21A and 21B illustrate the timing of an exemplary embodiment of the measurement and conversion process 1800 described with reference to FIG. 18.

Figure 19:
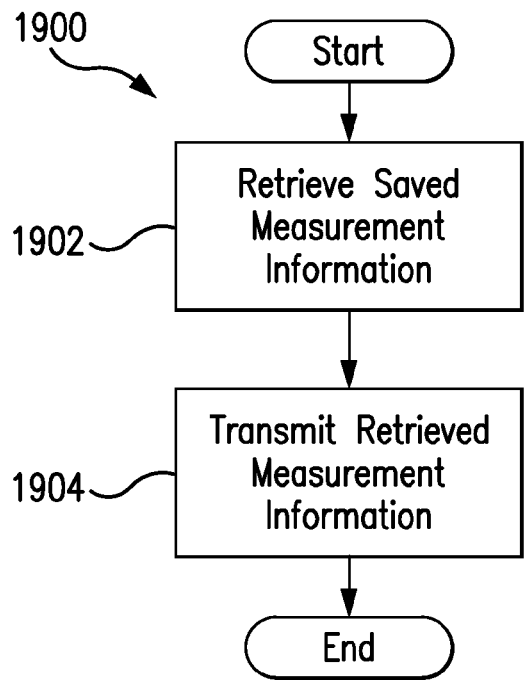
FIG. 19 illustrates a get result command execution process that may be performed by the optical sensor to execute a get result command received by the optical sensor in accordance with an embodiment of the present invention.

FIG. 19 illustrates a get result command execution process 1900 that may be performed in step 1604 of the sensor control process 1600 by the optical sensor 100 to execute a get result command received by the optical sensor 100 in accordance with an embodiment of the present invention. The measurement command execution process 1900 may begin with a step 1902 of retrieving saved measurement information. For example, retrieved measurement information may be saved during step 1712 of the measurement command execution process 1700 shown in FIG. 17. In some embodiments, measurement information is saved in the nonvolatile storage medium 660. In response to a request from the measurement controller 532, the nonvolatile storage medium 660 may output saved measurement information to the data and control bus 654. In some embodiments, the data and control bus 654 may transfer the retrieved measurement information to the measurement controller 532. However, in alternative embodiments, the data and control bus 654 may transfer the retrieved measurement information to the command decoder/data encoder 652 without first transferring the retrieved measurement information to the measurement controller 532.

In some embodiments, the nonvolatile storage medium 660 may output to the data and control bus 654 the measurement information most recently saved to the nonvolatile storage medium 660. In some alternative embodiments, the nonvolatile storage medium 660 may output to the data and control bus 654 the oldest measurement information most saved to the nonvolatile storage medium 660. In other alternative embodiments, the nonvolatile storage medium 660 may output to the data and control bus 654 the measurement information specifically requested by the measurement controller 532 (e.g., by an address sent to the nonvolatile storage medium 660 with a read request).

After the saved measurement information is retrieved, the get result command execution process 1900 may proceed to a step 1904 in which the sensor 100 may transmit the retrieved measurement information. In one embodiment, the measurement controller 532 may output the retrieved measurement information to the data and control bus 654. The data and control bus 654 may transfer the measurement information to the command decoder/data encoder 652, which may encode the retrieved measurement information. The data serializer 656 may serialize the encoded retrieved measurement information. The encoder 658 may encode the serialized retrieved measurement information. The clamp/modulator 646 may modulate the current flowing through the inductive element 114 (e.g., coil 220) as a function of the encoded retrieved measurement information. In this way, the encoded retrieved measurement information may be transmitted wirelessly by the inductive element 114 as a modulated electromagnetic wave. In some embodiments, the encoded retrieved measurement information wirelessly transmitted by the sensor 100 may be received by the sensor reader 1500.

Figure 20:
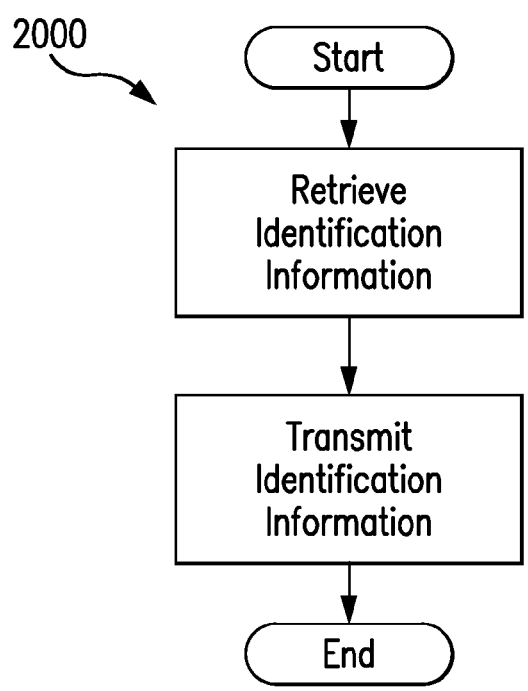
FIG. 20 illustrates a get identification information command execution process that may be performed by the optical sensor to execute a get identification information command received by the optical sensor in accordance with an embodiment of the present invention.

FIG. 20 illustrates a get identification information command execution process 2000 that may be performed in step 1604 of the sensor control process 1600 by the optical sensor 100 to execute a get identification information command received by the optical sensor 100 in accordance with an embodiment of the present invention. The get identification information command execution process 2000 may begin with a step 2002 of retrieving stored identification information. In some embodiments, identification information is stored in the nonvolatile storage medium 660. In response to a request from the measurement controller 532, the nonvolatile storage medium 660 may output identification information to the data and control bus 654. In some embodiments, the data and control bus 654 may transfer the retrieved identification information to the measurement controller 532. However, in alternative embodiments, the data and control bus 654 may transfer the retrieved identification information to the command decoder/data encoder 652 without first transferring the retrieved identification information to the measurement controller 532.

After the stored identification information is retrieved, the get identification information command execution process 2000 may proceed to a step 2004 in which the sensor 100 may transmit the retrieved identification information. In one embodiment, the measurement controller 532 may output the retrieved identification information to the data and control bus 654. The data and control bus 654 may transfer the identification information to the command decoder/data encoder 652, which may encode the identification information. The data serializer 656 may serialize the encoded identification information. The encoder 658 may encode the serialized identification information. The clamp/modulator 646 may modulate the current flowing through the inductive element 114 (e.g., coil 220) as a function of the encoded retrieved identification information. In this way, the encoded identification information may be transmitted wirelessly by the inductive element 114 as a modulated electromagnetic wave. In some embodiments, the encoded identification information wirelessly transmitted by the sensor 100 may be received by the sensor reader 1500.

The sensor 100 may be capable of executing other commands received by the sensor. For example, the sensor 100 may perform a setup parameter update execution process that may be performed in step 1604 of the sensor control process 1600 by the optical sensor 100 to execute a command to update setup parameters. In some embodiments, the setup parameter update execution process may replace one or more setup parameters (i.e., initialization information) stored in the nonvolatile storage medium 660. In one embodiment, upon receiving a command to update setup parameters, the measurement controller 532 may output one or more setup parameters received with the command to the data and control bus 654, which may transfer the setup parameter(s) to the nonvolatile storage medium 660. The nonvolatile storage medium 660 may store the received setup parameter(s). In a non-limiting embodiment, the received setup parameter(s) may replace one or more setup parameters previously stored in the nonvolatile storage medium 660.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A method of controlling an optical sensor, the method comprising:
   (a) wirelessly receiving, using an inductive element and an input/output circuit of the optical sensor, a measurement command and power, wherein the input/output circuit is fabricated in a semiconductor substrate of the optical sensor;
   (b) following receipt of the measurement command, using a measurement controller fabricated in the semiconductor substrate to turn a light source of the optical sensor on and off one or more times, wherein the light source is configured to, when turned on, irradiate indicator molecules having an optical characteristic responsive to a concentration of an analyte with excitation light, the indicator molecules being configured to interact with the analyte in a medium within a living animal;
   (c) while the light source is turned on, using the measurement controller to:
      (i) control a temperature transducer mounted on or fabricated in the semiconductor substrate to generate a first analog temperature measurement signal indicative of a temperature of the optical sensor;
      (ii) control a first photodetector mounted on or fabricated in the semiconductor substrate to generate a first analog light measurement signal indicative of the amount of light received by the first photodetector, wherein the light received by the first photodetector includes light emitted by the indicator molecules;
      (iii) control a second photodetector mounted on or fabricated in the semiconductor substrate to generate a second analog light measurement signal indicative of the amount of light received by the second photodetector; and
      (iv) control a comparator fabricated in the semiconductor substrate to generate an analog light difference measurement signal indicative of a difference between the first and second analog light measurement signals; and
   (d) while the light source is turned off, using the measurement controller to:
      (i) control the temperature transducer to generate a second analog temperature measurement signal indicative of a temperature of the optical sensor;
      (ii) control the first photodetector to generate a first analog ambient light measurement signal indicative of the amount of light received by the first photodetector; and
      (iii) control the second photodetector to generate a second analog ambient light measurement signal indicative of the amount of light received by the second photodetector;
   (e) while the light source is turned on or turned off, using the measurement controller to:
      (i) control an analog to digital converter (ADC) fabricated in the semiconductor substrate to convert the first analog temperature measurement signal to a first digital temperature measurement signal;
      (ii) control the ADC to convert the first analog light measurement signal to a first digital light measurement signal;
      (iii) control the ADC to convert the second analog light measurement signal to a second digital light measurement signal;
      (iv) control the ADC to convert the analog light difference measurement signal to a digital light difference measurement signal;
      (v) control the ADC to convert the second analog temperature measurement signal to a second digital temperature measurement signal;
      (vi) control the ADC to convert the first ambient analog light measurement signal to a first digital ambient light measurement signal; and
      (vii) control the ADC to convert the second analog ambient light measurement signal to a second digital ambient light measurement signal; and
   (f) transmitting, using the input/output circuit and the inductive element, (i) the first digital temperature measurement signal, (ii) the first digital light measurement signal, (iii) the second digital light measurement signal, (iv) the digital light difference measurement signal, (v) the second digital temperature measurement signal, (vi) the first digital ambient light measurement signal and (vii) the second digital ambient light measurement signal.

2. The method of claim 1, wherein the optical sensor is a chemical or biochemical sensor.

3. The method of claim 1, further comprising:
   reading calibration information stored in a nonvolatile storage medium fabricated in the semiconductor substrate; and
   controlling the light source in accordance with the calibration information.

4. The method of claim 1, further comprising transmitting, using the input/output circuit and inductive element, identification information stored in a nonvolatile storage medium fabricated in the semiconductor substrate.

5. The method of claim 1, further comprising using a field strength measurement circuit to determine whether a current produced from the wirelessly received power is above a threshold.

6. The method of claim 1, wherein the indicator molecules are signal channel indicator molecules, and the method further comprises:
   irradiating the signal channel indicator molecules and reference channel indicator molecules of the optical sensor with excitation light emitted by the light source when turned on, wherein the reference channel indicator molecules are configured to not interact with the analyte in the medium within the living animal;
   receiving, by the first photodetector, light emitted by the signal channel indicator molecules; and
   receiving, by the second photodetector, light emitted by the reference channel indicator molecules.

7. The method of claim 1, wherein the living animal is a living human being.

8. The method of claim 1, wherein the medium is interstitial fluid.

9. The method of claim 8, wherein the analyte is glucose.

10. The method of claim 8, wherein the analyte is oxygen.

11. The method of claim 1, wherein the medium is blood.

12. The method of claim 1, wherein the indicator molecules are fluorescent indicator molecules.

* * * * *